(12) United States Patent
Konno

(10) Patent No.: US 12,042,312 B2
(45) Date of Patent: Jul. 23, 2024

(54) MAMMOGRAPHY APPARATUS

(71) Applicant: FUJIFILM CORPORATION, Tokyo (JP)

(72) Inventor: Shinichiro Konno, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 263 days.

(21) Appl. No.: 17/505,639

(22) Filed: Oct. 20, 2021

(65) Prior Publication Data

US 2022/0133247 A1 May 5, 2022

(30) Foreign Application Priority Data

Oct. 29, 2020 (JP) ................................ 2020-181852

(51) Int. Cl.
*A61B 6/04* (2006.01)
*A61B 6/50* (2024.01)

(52) U.S. Cl.
CPC ............ *A61B 6/0414* (2013.01); *A61B 6/502* (2013.01)

(58) Field of Classification Search
CPC ........... A61B 6/00; A61B 6/04; A61B 6/0414; A61B 6/502; A61B 6/54
See application file for complete search history.

(56) References Cited

U.S. PATENT DOCUMENTS

| | | | |
|---|---|---|---|
| 2014/0348291 A1 | 11/2014 | Lee et al. | |
| 2016/0135772 A1 | 5/2016 | Nam et al. | |
| 2016/0166222 A1 | 6/2016 | Kim | |
| 2017/0367671 A1 | 12/2017 | Arai et al. | |
| 2017/0367674 A1* | 12/2017 | Arai | ............... A61B 6/54 |

FOREIGN PATENT DOCUMENTS

| | | |
|---|---|---|
| EP | 3263035 A1 | 1/2018 |
| JP | H04-64346 A | 2/1992 |
| JP | 2004-57833 A | 2/2004 |
| JP | 2010-179030 A | 8/2010 |
| JP | 2017-225634 A | 12/2017 |
| WO | 2019226792 A1 | 11/2019 |
| WO | 2020-068845 A1 | 4/2020 |

OTHER PUBLICATIONS

Partial European Search Report dated Mar. 10, 2022, issued in corresponding EP Patent Application No. 21204434.1.
Extended European Search Report dated Jun. 2, 2022, issued in corresponding EP Patent Application No. 21204434.1.
English language translation of the following: Office action dated Feb. 20, 2024 from the JPO in a Japanese patent application No. 2020-181852 corresponding to the instant patent application. This office action translation is submitted now in order to supplement the understanding of the cited references which are being disclosed in the instant Information Disclosure Statement.

* cited by examiner

*Primary Examiner* — Jurie Yun
(74) *Attorney, Agent, or Firm* — SOLARIS Intellectual Property Group, PLLC

(57) ABSTRACT

A mammography apparatus includes an imaging table on which a breast of a subject is placed, a compression plate that compresses the breast, the compression plate being disposed to face the imaging table and being movable in a vertical direction with respect to the imaging table, and an operation portion that is operated to move the compression plate, the operation portion being provided separately from the compression plate and being displaced along a movement direction of the compression plate.

18 Claims, 29 Drawing Sheets

$H_1 > H_2$ → $Vi_{1d} < Vi_{2d}$ $H_1 > H_2 \rightarrow Vi_{1u} < Vi_{2u}$

MAMMOGRAPHY APPARATUS

CROSS-REFERENCE TO RELATED APPLICATIONS

The present application claims priority under 35 U.S.C. § 119 to Japanese Patent Application No. 2020-181852, filed on Oct. 29, 2020. The above application is hereby expressly incorporated by reference, in its entirety, into the present application.

BACKGROUND

1. Technical Field

The technology of the present disclosure relates to a mammography apparatus.

2. Description of the Related Art

A mammography apparatus is known that irradiates a breast of a subject with radiation and captures a radiation image of the breast. The mammography apparatus is provided with an imaging table on which the breast is placed and a compression plate which is disposed to face the imaging table and compresses the breast. The compression plate can be raised and lowered in a vertical direction with respect to the imaging table, and the breast is compressed by lowering the compression plate toward the imaging table. As an operation portion operated to raise and lower the compression plate, a button operation portion, a pedal operation portion, a rotation operation portion, and the like are known. The button operation portion and the pedal operation portion have two buttons or two foot pedals corresponding to a raising instruction and a lowering instruction, and are operated by a pressing operation of the button or a depressing operation of the pedal.

The rotation operation portion includes a rotation knob, a jog dial, or the like. The rotation operation portion can rotate in two rotation directions, a clockwise direction and a counterclockwise direction, and the two rotation directions are assigned to the raising instruction or the lowering instruction, respectively. A mammography apparatus disclosed in JP2004-57833A is provided with a handle in a form of a rotation knob as an operation portion that raises and lowers a pad (corresponding to a compression plate) that presses a chest (corresponding to a breast). By rotating the handle, the pad is raised and lowered.

SUMMARY

In each of the operation portions described in Description of the Related Art, the operation direction is not along a movement direction of the compression plate in the vertical direction. For example, the operation directions of the pressing operation of the button or the depressing operation of the pedal, and the rotation operation of the rotation knob or the jog dial are all significantly different from the vertical direction, which is the movement direction of the raising and lowering operation of the compression plate. In a case in which the operation direction of the operation portion is not along the movement direction of the compression plate as described above, it is difficult to understand a correspondence between the operation direction of the operation portion and the movement direction of the compression plate. In a case in which the correspondence is difficult to understand, it is necessary for an operator to confirm the correspondence for each operation, such as which of the two buttons is pressed to raise or lower the compression plate or which way to turn the rotation knob to raise or lower the compression plate, and thus there is a problem of poor operability, such as the need to move the compression plate slightly on a trial basis to confirm the movement direction.

The present disclosure is to provide a mammography apparatus having better operability of a compression plate than the related art.

A mammography apparatus according to the present disclosure comprises an imaging table on which a breast of a subject is placed, a compression plate that compresses the breast, the compression plate being disposed to face the imaging table and being movable in a vertical direction with respect to the imaging table, and an operation portion that is operated to move the compression plate, the operation portion being provided separately from the compression plate and being displaced along a movement direction of the compression plate.

It is preferable that the mammography apparatus further comprise a support portion that supports the compression plate to be movable with respect to the imaging table, in which the operation portion is provided on the support portion.

It is preferable that the mammography apparatus further comprise a support portion that supports the compression plate to be movable with respect to the imaging table, and a movable portion that is disposed between the compression plate and the support portion and is moved in the vertical direction together with the compression plate, in which the operation portion is provided on the movable portion.

It is preferable that the mammography apparatus further comprise an actuator that drives the compression plate, in which the actuator is activated in response to an operation of the operation portion, and the compression plate is moved by driving force generated by the actuator.

It is preferable that the mammography apparatus further comprise a processor that controls the actuator to change a movement speed of the compression plate.

It is preferable that the mammography apparatus further comprise a displacement amount detection unit that detects a displacement amount of the operation portion, in which the processor changes the movement speed of the compression plate based on the displacement amount detected by the displacement amount detection unit.

It is preferable that the mammography apparatus further comprise a height detection unit that detects a height of the compression plate with respect to the imaging table, in which the processor changes the movement speed of the compression plate in response to the height of the compression plate.

It is preferable that the processor set an initial speed of the compression plate in a case in which the compression plate is raised from a state in which the compression plate is positioned at a relatively low position to be faster than an initial speed of the compression plate in a case in which the compression plate is raised from a state in which the compression plate is positioned at a relatively high position.

It is preferable that the processor set an initial speed of the compression plate in a case in which the compression plate is lowered from a state in which the compression plate is positioned at a relatively high position to be faster than an initial speed of the compression plate in a case in which the compression plate is lowered from a state in which the compression plate is positioned at a relatively low position.

It is preferable that the mammography apparatus further comprise a displacement speed detection unit that detects a displacement speed of the operation portion, in which the processor sets the movement speed of the compression plate to be faster as the displacement speed of the operation portion is faster.

It is preferable that the mammography apparatus further comprise a pressure detection unit that detects a pressure received by the compression plate from the breast.

It is preferable that the processor set a rate of change in speed, which is a ratio of a change amount of the movement speed of the compression plate to a unit displacement amount of the operation portion, to be smaller as the pressure is larger.

It is preferable that the processor stop movement of the compression plate in a case in which the pressure detected by the pressure detection unit is equal to or larger than a preset threshold value.

It is preferable that the mammography apparatus further comprise a load increasing unit that increases a load for operating the operation portion as a displacement amount of the operation portion is larger.

It is preferable that the operation portion be a cantilever type lever having one end, which is a free end, and at least the free end be displaced along the movement direction of the compression plate.

It is preferable that assuming that a direction of a position of the subject who places the breast on the imaging table is anterior and an opposite direction thereof is posterior, the operation portion stretch in an anteroposterior direction or a lateral direction.

It is preferable that the operation portion rotate about a fulcrum provided on a base end side.

It is preferable that the operation portion include a main shaft portion that extends from the base end side to a free end side, and a protruding portion that is provided on the main shaft portion and protrudes to at least one of a lower side or an upper side with an axial direction of the main shaft portion as a reference.

It is preferable that the protruding portion include a first protruding portion that protrudes to the lower side of the main shaft portion, and a second protruding portion that protrudes to the upper side of the main shaft portion.

It is preferable that the protruding portion have a hook shape or a ring shape.

According to the technology of the present disclosure, it is possible to provide a mammography apparatus having better operability of the compression plate than the related art.

BRIEF DESCRIPTION OF THE DRAWINGS

Exemplary embodiments according to the technique of the present disclosure will be described in detail based on the following figures, wherein.

DESCRIPTION OF THE PREFERRED EMBODIMENTS

First Embodiment

Figure 1:
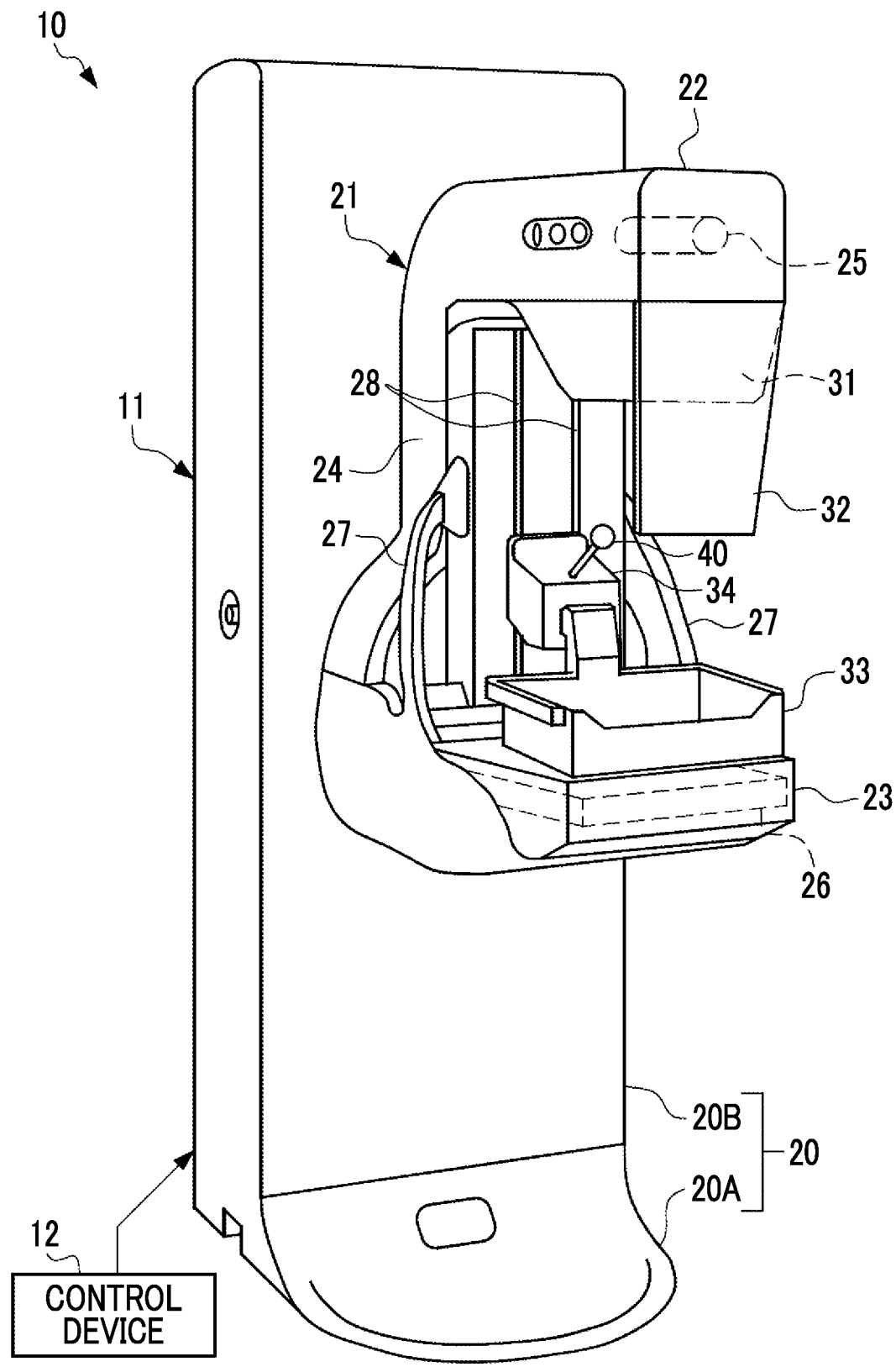
FIG. 1 is a perspective view showing an example of an overall configuration of a mammography apparatus according to a first embodiment.

FIG. 1 shows an example of an overall configuration of a mammography apparatus according to a first embodiment. A mammography apparatus 10 uses a breast M of a subject (see FIG. 3) as an object. The mammography apparatus 10 is a radiography apparatus that irradiates the breast M with radiation (for example, X-rays or y-rays) and captures a radiation image of the breast M.

The mammography apparatus 10 comprises an apparatus body 11 and a control device 12. The apparatus body 11 is installed in a radiography room of a medical facility, for example. The control device 12 is installed in a control room adjacent to the radiography room, for example. The control device 12 is a desktop-type personal computer, for example. The control device 12 is communicably connected to an image database server (not shown) via a network (not shown) such as a local area network (LAN).

The apparatus body 11 includes a stand 20 and an arm 21. The stand 20 is configured by a seat 20A installed on a floor of the radiography room and a support column 20B extending in a height direction from the seat 20A. The arm 21 has a substantially C-shape as viewed from the side, and is connected to the support column 20B. Since the arm 21 is movable in the height direction with respect to the support column 20B, a height thereof can be adjusted in response to a height of the subject. In addition, the arm 21 can rotate around a rotation shaft perpendicular to the support column 20B.

The arm 21 is configured by a radiation source housing portion 22, an imaging table 23, and a body portion 24. A radiation source 25 is housed in the radiation source housing portion 22. The breast M of the subject is placed on the imaging table 23. A radiation detector 26 is housed in the imaging table 23. The body portion 24 integrally connects the radiation source housing portion 22 and the imaging table 23. The body portion 24 holds the radiation source housing portion 22 and the imaging table 23 at facing positions. Handrails 27 held by the subject by the hands are provided on the both sides of the body portion 24.

The radiation source 25 irradiates the breast M placed on the imaging table 23 with the radiation. The radiation emitted from the radiation source 25 is transmitted through a compression plate 33 and then incident on the breast M. The radiation detector 26 detects the radiation transmitted through the breast M and outputs the radiation image. The radiation detector 26 is called a flat panel detector (FPD). The radiation detector 26 may include a scintillator that converts the radiation into visible light, and may be an indirect conversion type that converts the visible light emitted by the scintillator into an electric signal, or a direct conversion type that directly converts the radiation into an electric signal.

An irradiation field limiter 31 is provided between the radiation source housing portion 22 and the imaging table 23. The irradiation field limiter 31 is also called a collimator, and defines an irradiation field of the radiation to the imaging table 23.

A face guard 32 is attached to the radiation source housing portion 22. The face guard 32 is made or coated with a material through which the radiation is not transmitted, and protects a face of the subject from the radiation.

The compression plate 33, which interposes and compresses the breast M with the imaging table 23, is provided between the imaging table 23 and the irradiation field limiter 31. The compression plate 33 is made of a material through which the radiation is transmitted. The compression plate 33 is disposed at a position facing the imaging table 23. In the present embodiment, the compression plate 33 has a box shape with an open upper surface side. The compression plate 33 may have another shape, such as a flat plate shape.

The body portion 24 of the arm 21 supports the compression plate 33 to be movable with respect to the imaging table 23. The body portion 24 is an example of a "support portion" according to the technology of the present disclosure. In addition, a movable portion 34 is disposed between the compression plate 33 and the body portion 24. The movable portion 34 is held by a rail 28 provided on the body portion 24 to be movable slidingly. The rail 28 stretches in a vertical direction.

The compression plate 33 is attached to the movable portion 34. The movable portion 34 is moved in the vertical direction together with the compression plate 33 by a drive mechanism, which will be described below. Functionally, the vertical direction is a direction in which the compression plate 33 is moved toward the imaging table 23 (downward direction) and a direction in which the compression plate 33 is separated from the imaging table 23 (upward direction). As described above, the compression plate 33 is configured to be movable with respect to the imaging table 23.

Figure 2:
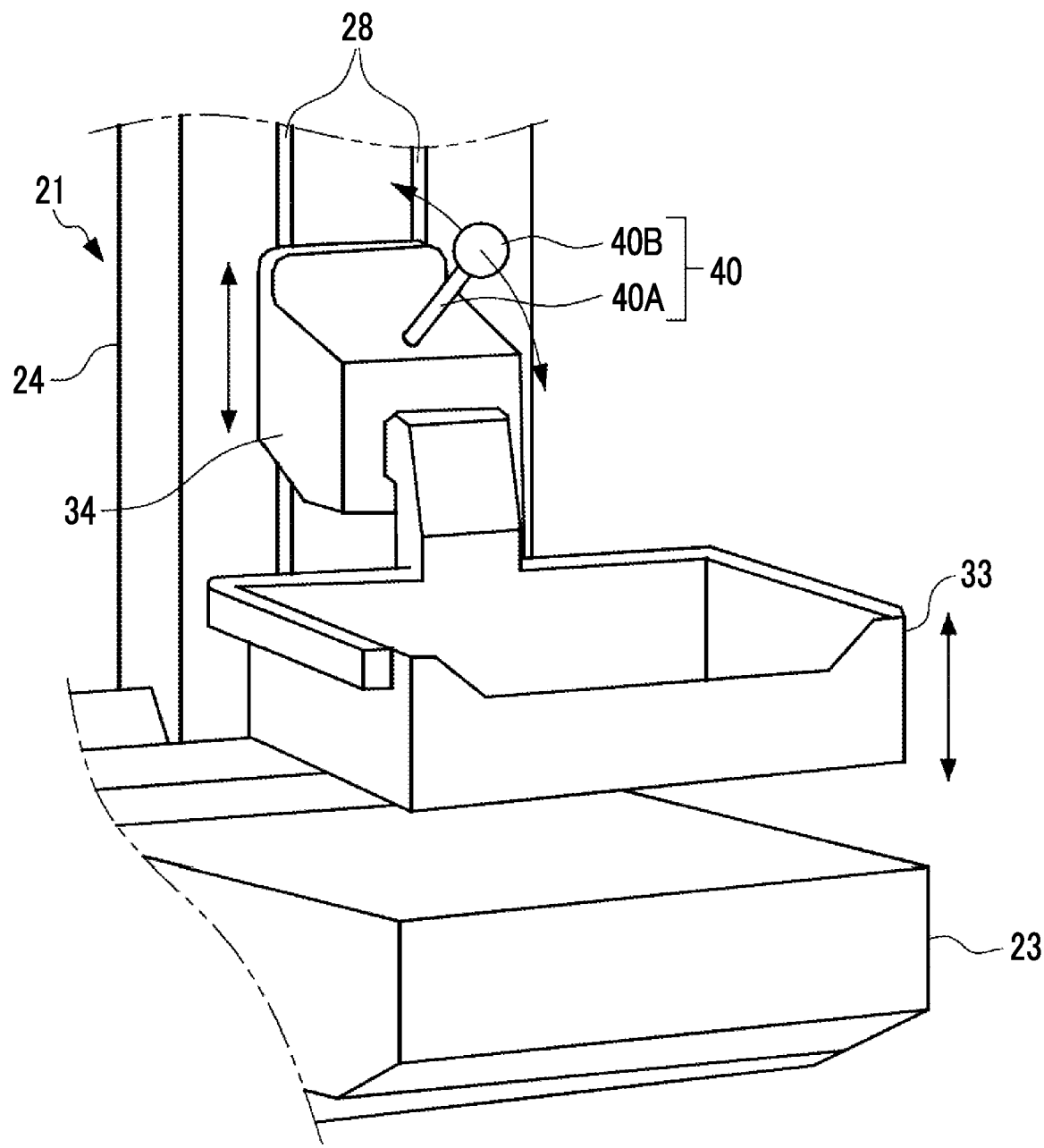
FIG. 2 is a partially enlarged view of the mammography apparatus.

FIG. 2 is a partially enlarged view of the mammography apparatus 10. As shown in FIG. 2, the mammography apparatus 10 is provided with an operation portion 40 that moves the compression plate 33 in the vertical direction. The operation portion 40 is provided separately from the compression plate 33, and is displaced along a movement direction of the compression plate 33. In the present embodiment, the operation portion 40 is provided on the movable portion 34.

The operation portion 40 is operated in a case in which an operator, such as a radiologist, compresses the breast with respect to the imaging table 23 with the compression plate 33 to perform positioning of the breast M during radiography. In addition, the operation portion 40 is operated in a case in which the operator releases the compression of the breast M by the compression plate 33 after the radiography is terminated.

Figure 3:
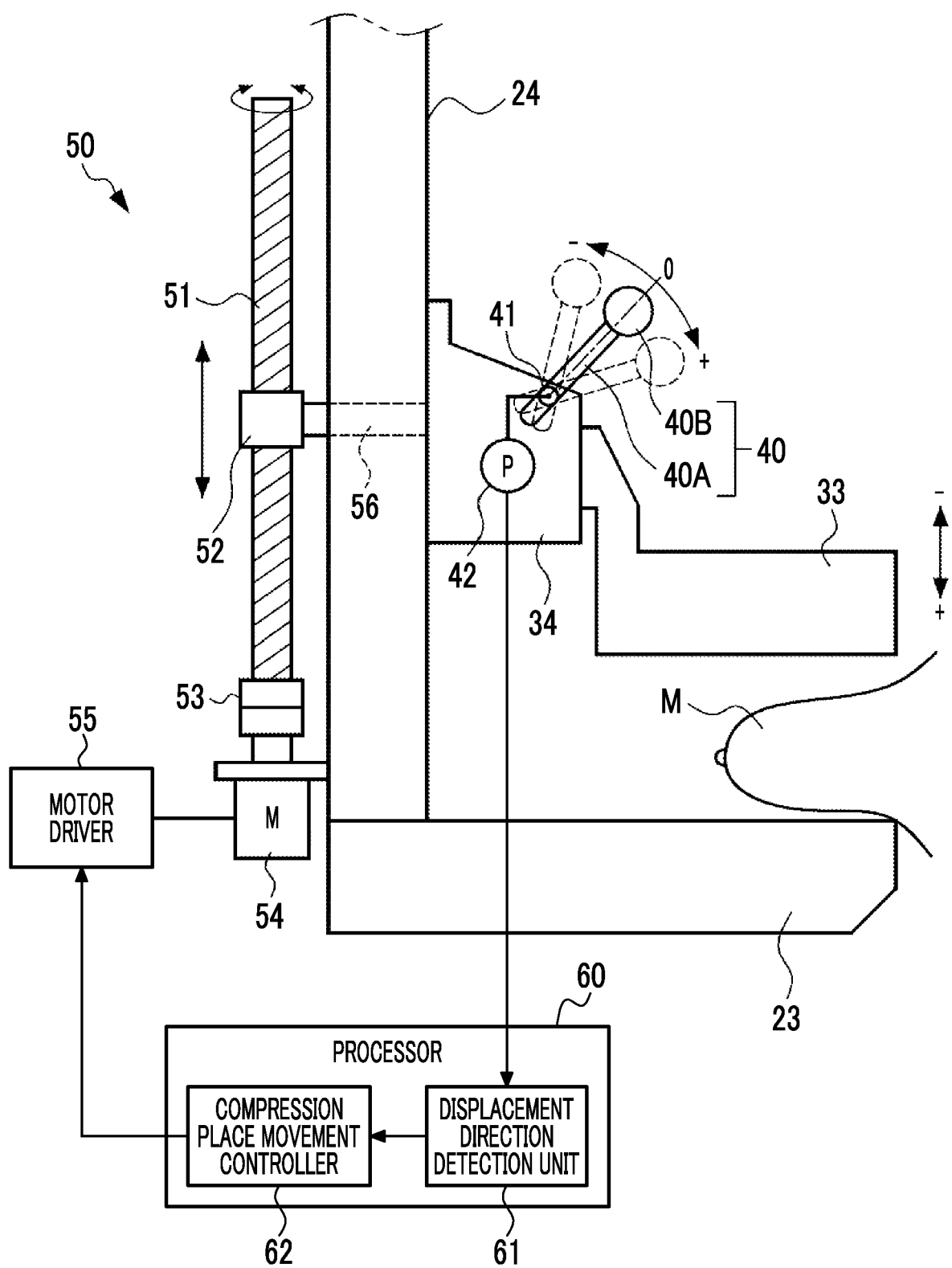
FIG. 3 is a view showing an example of configurations of a drive mechanism of a compression plate and a processor.

As shown in FIG. 3, the operation portion 40 is a cantilever type lever having one end, which is a free end, and the free end is displaced along the movement direction of the compression plate 33. In the present embodiment, the operation portion 40 is configured by a rod-shaped main shaft portion 40A and a spherical-shaped grip portion 40B. The grip portion 40B is attached to one end (that is, free end) of the main shaft portion 40A. A rotation shaft 41 is provided at the other end (that is, base end) of the main shaft portion 40A. The rotation shaft 41 is disposed inside the movable portion 34.

The operation portion 40 is attached to the movable portion 34 such that the main shaft portion 40A stretches toward a side of the subject who places the breast M on the imaging table 23. In the present embodiment, the main shaft portion 40A obliquely stretches in the upward direction toward the side of the subject. That is, assuming that a direction of a position of the subject who places the breast on the imaging table 23 is anterior and an opposite direction thereof is posterior, the operation portion 40 having a lever shape stretches in an anteroposterior direction. In the mammography apparatus 10, assuming that a stand 20 side is posterior and a direction in which the imaging table 23 protrudes is anterior, the anteroposterior direction is, in other words, a depth direction of the mammography apparatus 10, and the operation portion 40 stretches in the depth direction of the mammography apparatus 10. Here, the anteroposterior direction, which is a stretching direction of the operation portion 40, is a concept including a case other than a case of being parallel to the floor (horizontal plane) as in the present example, and does not include a width direction and a perpendicular direction of the mammography apparatus 10. Specifically, in a case of being defined by an angle with the horizontal plane as a reference, the stretching direction of the operation portion 40 at a neutral position (position indicated by a solid line in FIG. 3) in a state of not being operated is about 60° or less with respect to the horizontal plane, preferably 45° or less as in the present example.

The operation portion 40 rotates with the rotation shaft 41 provided on a base end side as a fulcrum. The grip portion 40B is displaced in a direction along the movement direction of the compression plate 33, that is, in the vertical direction. The operator can displace the grip portion 40B in the vertical direction in a state of gripping the grip portion 40B. In a case in which the grip portion 40B is displaced in the downward direction, the compression plate 33 is moved (that is, lowered) toward the imaging table 23. In a case in which the grip portion 40B is displaced in the upward direction, the compression plate 33 moves (that is, raised) in a direction separated from the imaging table 23.

Further, FIG. 3 shows an example of configurations of the drive mechanism of the compression plate 33 and a processor that controls movement of the compression plate 33. A drive mechanism 50 shown in FIG. 3 is a so-called electric linear actuator. The drive mechanism 50 is provided, for example, inside the body portion 24 and is activated by an operation of the operation portion 40.

The drive mechanism 50 includes a rod screw 51, a nut 52, a coupling 53, a motor 54, and a motor driver 55. The rod screw 51 extends in the vertical direction along the rail 28 (see FIG. 2). The rod screw 51 is a trapezoidal screw, for example. The nut 52 is screwed with the rod screw 51. The movable portion 34 is connected to the nut 52 via a connection portion 56. The movable portion 34 is moved in the vertical direction together with the nut 52 by rotation of the rod screw 51.

The motor 54 is connected to the rod screw 51 via the coupling 53. The motor 54 is driven by the motor driver 55 and rotates the rod screw 51 via the coupling 53. A rotation direction of the rod screw 51 corresponds to the movement direction of the movable portion 34. For example, in a case in which the rod screw 51 rotates clockwise, the movable portion 34 is lowered, and in a case in which the rod screw 51 rotates counterclockwise, the movable portion 34 is raised. In addition, a rotation speed of the rod screw 51 corresponds to a movement speed of the movable portion 34.

As described above, the compression plate 33 is moved together with the movable portion 34 by driving force generated by the drive mechanism 50 as the actuator.

A processor 60 is configured by, for example, a central processing unit (CPU), a memory, and the like. The processor 60 realizes various functions by executing a process by the CPU based on a program stored in the memory. The processor 60 is provided, for example, inside the body portion 24.

In the present embodiment, the processor 60 includes a displacement direction detection unit 61 and a compression plate movement controller 62. The displacement direction detection unit 61 detects a displacement direction of the operation portion 40 based on a detection signal output from a potentiometer 42 as an angle detection sensor connected to the rotation shaft 41 of the operation portion 40. The potentiometer 42 is provided inside the movable portion 34, and outputs the detection signal in response to an angle of the operation portion 40. Note that it is also possible to use an encoder as the angle detection sensor instead of the potentiometer 42.

In FIG. 3, a state in which the operation portion 40 is positioned at the neutral position is shown by the solid line. For example, the displacement direction detection unit 61 detects a case in which the grip portion 40B of the operation portion 40 is displaced in the downward direction from the neutral position as "displacement in a positive direction" and detects a case in which the grip portion 40B of the operation portion 40 is displaced in the upward direction from the neutral position as "displacement in a negative direction", and detects whether the displacement direction is positive or negative.

The compression plate movement controller 62 controls the drive mechanism 50 based on the displacement direction detected by the displacement direction detection unit 61. Specifically, the compression plate movement controller 62 controls the motor driver 55 in response to the displacement direction detected by the displacement direction detection unit 61 to change a rotation direction of the motor 54. In a case in which the displacement direction is the positive direction (that is, downward direction), the compression plate movement controller 62 lowers the compression plate 33 together with the movable portion 34 by rotating the motor 54 clockwise. In addition, in a case in which the displacement direction is the negative direction (that is, upward direction), the compression plate movement controller 62 raises the compression plate 33 together with the movable portion 34 by rotating the motor 54 counterclockwise.

Figure 4:
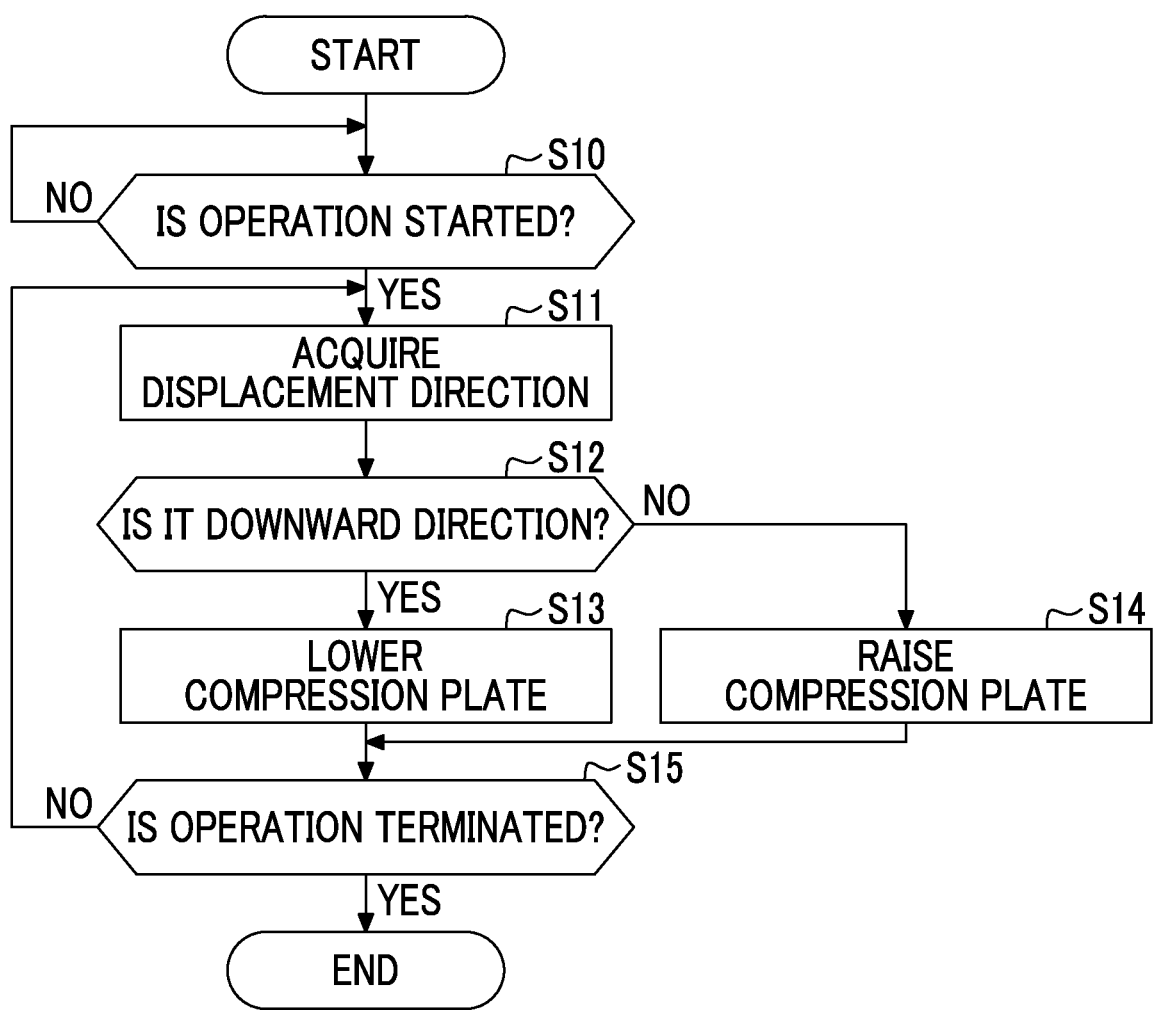
FIG. 4 is a flowchart showing an example of a movement control of the compression plate.

Next, an example of a movement control of the compression plate 33 by the compression plate movement controller 62 will be described with reference to a flowchart shown in FIG. 4. First, the compression plate movement controller 62 determines whether or not the operation of the operation portion 40 is started (step S10). For example, the compression plate movement controller 62 determines that the operation of the operation portion 40 is started in a case in which the operation portion 40 is displaced from the neutral position.

In a case in which it is determined that the operation of the operation portion 40 is started (step S10: YES), the compression plate movement controller 62 acquires the displacement direction detected by the displacement direction detection unit 61 (step S11). The compression plate movement controller 62 determines whether or not the acquired displacement direction is the downward direction (step S12). In a case in which it is determined that the displacement direction is the downward direction (step S12: YES), the compression plate movement controller 62 controls the drive mechanism 50 to lower the compression plate 33 (step S13). On the other hand, in a case in which it is determined that the displacement direction is the upward direction (step S12: NO), the compression plate movement controller 62 controls the drive mechanism 50 to raise the compression plate 33 (step S14).

After executing step S13 or step S14, the compression plate movement controller 62 determines whether or not the operation of the operation portion 40 is terminated (step S15). For example, the compression plate movement controller 62 determines that the operation of the operation portion 40 is terminated in a case in which the operation portion 40 is returned to the neutral position. In a case in which it is determined that the operation of the operation portion 40 is not terminated (step S15: NO), the compression plate movement controller 62 returns the process to step S11.

The compression plate movement controller 62 repeats the processes of steps S11 to S15 until it is determined that the operation of the operation portion 40 is terminated, and terminates the process in a case in which it is determined that the operation of the operation portion 40 is terminated (step S15: YES).

In a case in which the compression plate 33 is lowered to compress the breast M, the operator who operates the operation portion 40 need only operate the operation portion 40 in a direction in which the compression plate 33 is lowered. On the contrary, in a case in which the compression plate 33 is raised to release the compression of the breast M, the operator who operates the operation portion 40 need only operate the operation portion 40 in a direction in which the compression plate 33 is raised.

As described above, in the present embodiment, the operation portion is displaced along the movement direction of the compression plate, and thus the operation direction of the operation portion and the movement direction of the compression plate are substantially the same. Therefore, the operator can intuitively operate the operation portion. That is, the mammography apparatus according to the present embodiment has better operability of the compression plate as compared with an apparatus in the related art in which the operation direction of the operation portion and the movement direction of the compression plate are significantly different. Therefore, according to the technology of the present disclosure, it is possible to provide the mammography apparatus having better operability of the compression plate than the related art.

Second Embodiment

Next, a mammography apparatus according to a second embodiment will be described. The second embodiment is different from the first embodiment only in a functional configuration of the processor 60.

Figure 5:
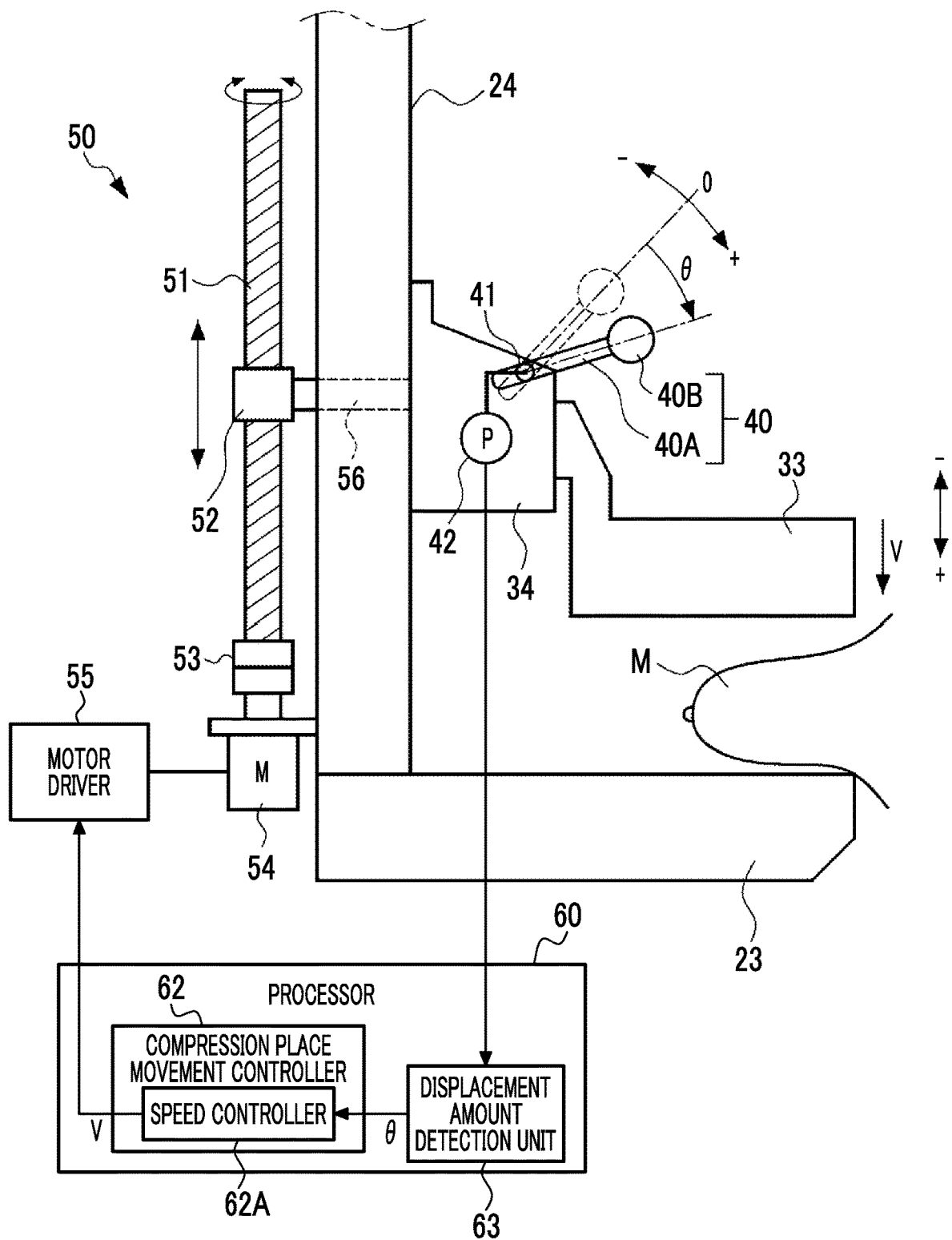
FIG. 5 is a view showing a configuration of a mammography apparatus according to a second embodiment.

FIG. 5 shows a configuration of the mammography apparatus according to the second embodiment. As shown in FIG. 5, in the present embodiment, the processor 60 includes a displacement amount detection unit 63 and the compression plate movement controller 62. In addition, the compression plate movement controller 62 includes a speed controller 62A.

The displacement amount detection unit 63 detects an angle θ of the operation portion 40 based on the detection signal output from the potentiometer 42. In FIG. 5, the state in which the operation portion 40 is positioned at the neutral position is shown by a broken line. The angle θ represents a rotation angle of the operation portion 40 from the neutral position. For example, the angle θ has a "positive value" in a case in which the grip portion 40B of the operation portion 40 is displaced in the downward direction from the neutral position, and has a "negative value" in a case in which the grip portion 40B of the operation portion 40 is displaced in the upward direction from the neutral position. That is, the angle θ is a concept including the "displacement direction" described in the first embodiment. Note that the angle θ is an example of a "displacement amount" according to the technology of the present disclosure.

The speed controller 62A obtains a speed V corresponding to the angle θ as the displacement amount detected by the displacement amount detection unit 63, and controls the motor driver 55 such that the compression plate 33 is moved at the obtained speed V. For example, the speed V has a "positive value" in a case in which the compression plate 33 is lowered, and has a "negative value" in a case in which the compression plate 33 is raised. That is, the speed V is a concept including the "movement direction" described in the first embodiment. The speed controller 62A controls a rotation speed (including the rotation direction) of the motor 54 via the motor driver 55 to change the speed V at which the compression plate 33 is moved.

Figure 6:
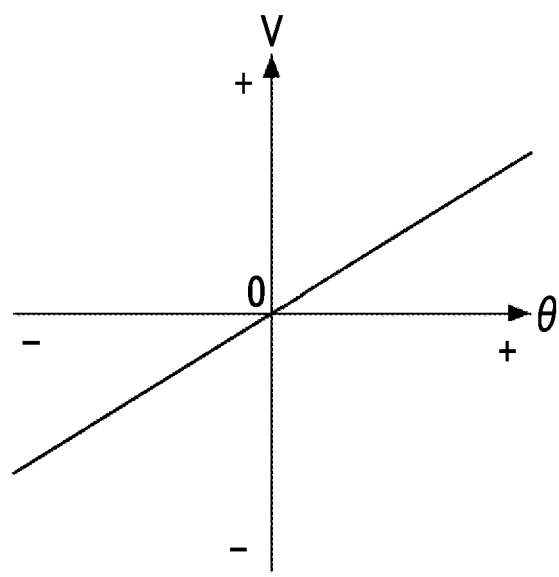
FIG. 6 is a graph showing an example of a relationship between an angle and a speed.

FIG. 6 shows an example of a relationship between the angle θ and the speed V. In FIG. 6, the speed V has a proportional relationship with the angle θ. The speed controller 62A obtains the speed V corresponding to the angle θ detected by the displacement amount detection unit 63 based on the relationship between the angle θ and the speed V shown in FIG. 6. Note that the speed controller 62A may store the relationship between the angle θ and the speed V as a function to obtain the speed V based on the function. In addition, the speed controller 62A may store the relationship between the angle θ and the speed V in the memory as a look up table (LUT), and obtain the speed V based on the LUT.

In a case in which the speed controller 62A performs a speed control using the relationship between the angle θ and the speed V shown in FIG. 6, the speed V of the compression plate 33 is changed in proportion to the displacement amount of the operation portion 40. That is, a rate of change in the speed V of the compression plate 33 with respect to a unit displacement amount of the operation portion 40 is fixed.

Figure 7:
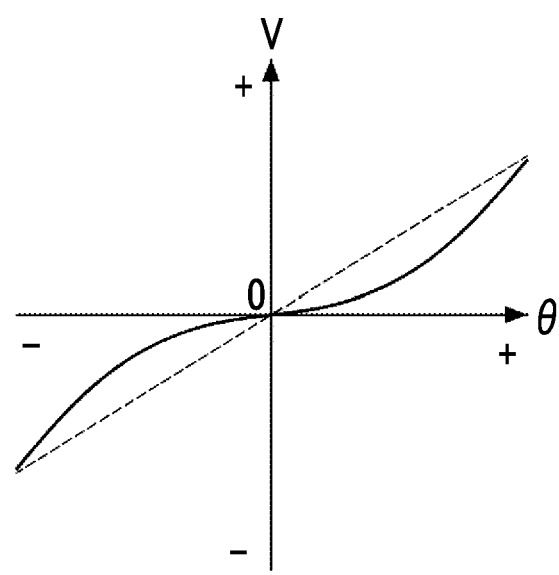
FIG. 7 is a graph showing another example of the relationship between the angle and the speed.

FIG. 7 shows another example of the relationship between the angle θ and the speed V. In FIG. 7, a relationship between the speed V and the angle θ is non-linear, and the rate of change in the speed V is larger as the angle θ is larger. The speed V is changed with respect to the angle θ at a rate of change such as an exponential function, for example.

In a case in which the speed controller 62A performs a speed control using the relationship between the angle θ and the speed V shown in FIG. 7, the rate of change in the speed V of the compression plate 33 is increased as the displacement amount of the operation portion 40 is larger.

Figure 8:
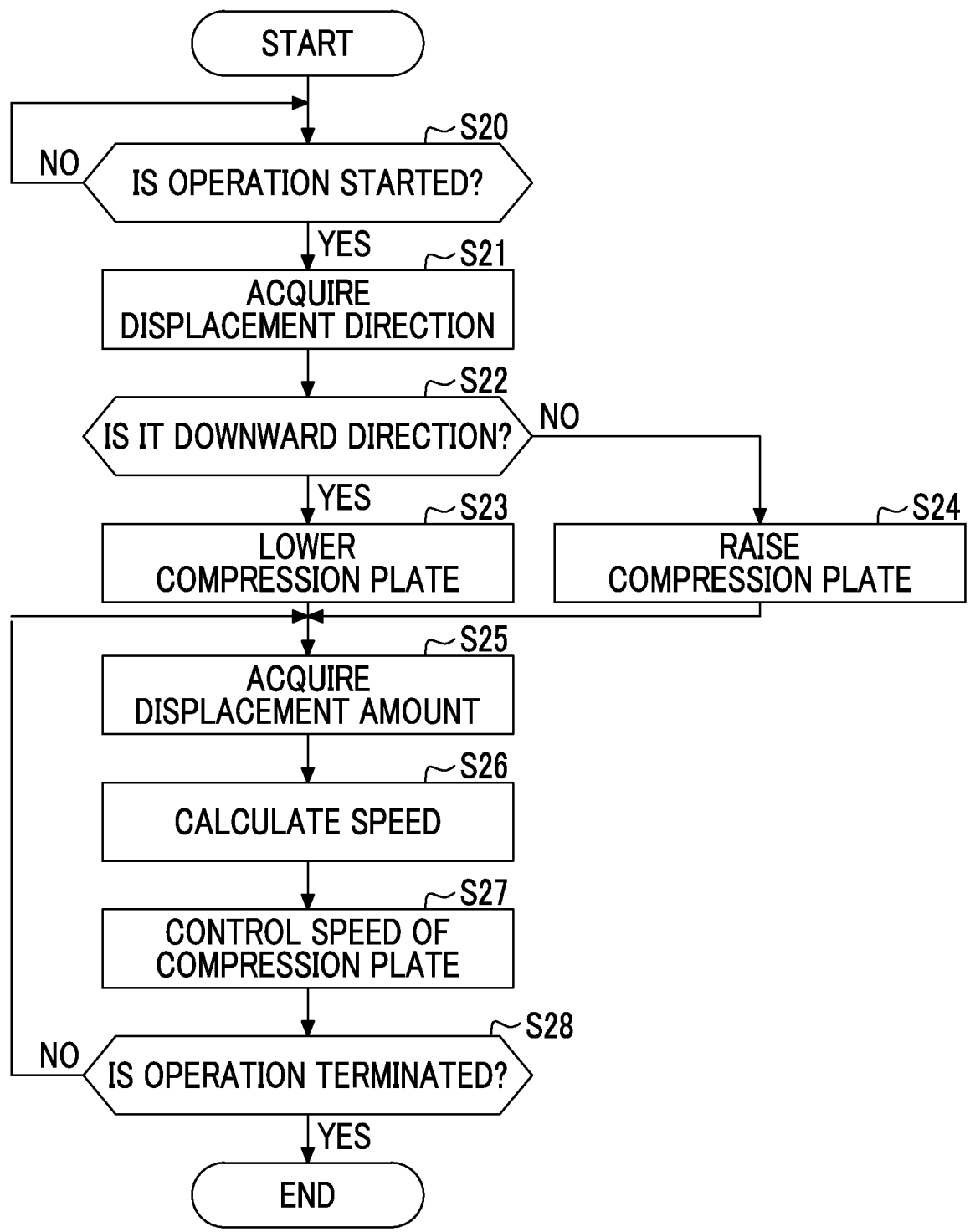
FIG. 8 is a flowchart showing an example of a movement control according to the second embodiment.

Next, an example of a movement control of the compression plate 33 according to the present embodiment will be described with reference to a flowchart shown in FIG. 8. Steps S20 to S24 shown in FIG. 8 are the same as steps S10 to S14 shown in FIG. 4, and thus the description thereof will be omitted.

After step S23 or step S24, the compression plate movement controller 62 acquires the angle θ as the displacement amount detected by the displacement amount detection unit 63 (step S25). The speed controller 62A obtains the speed V based on the angle θ acquired by the compression plate movement controller 62 (step S26). Then, the speed controller 62A controls the drive mechanism 50 such that the compression plate 33 is moved at the obtained speed V (step S27).

Thereafter, the compression plate movement controller 62 determines whether or not the operation of the operation portion 40 is terminated (step S28). In a case in which it is determined that the operation of the operation portion 40 is not terminated (step S28: NO), the compression plate movement controller 62 returns the process to step S25. In a case in which it is determined that the operation of the operation portion 40 is terminated (step S28: YES), the compression plate movement controller 62 terminates the process.

Figure 9:
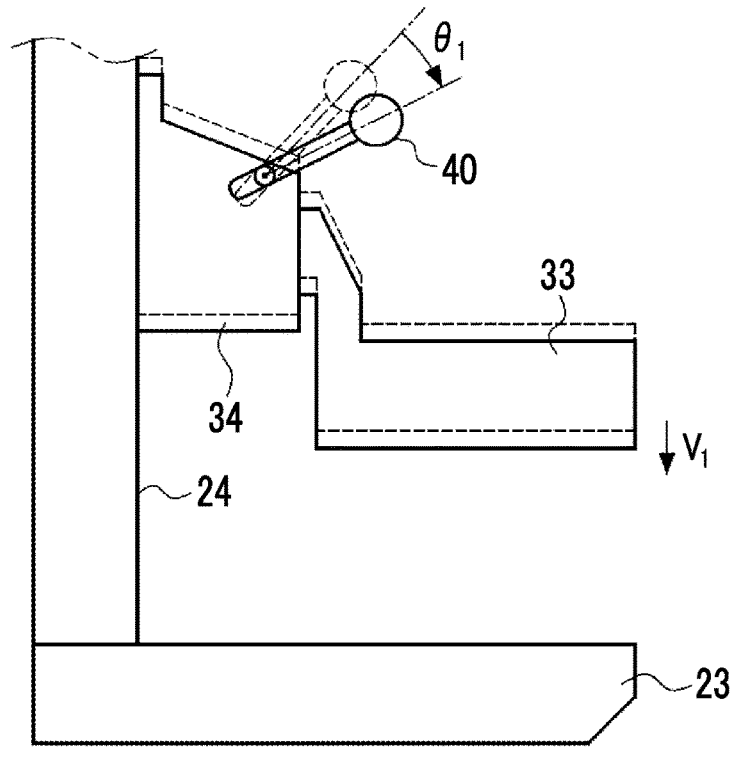
FIG. 9 is a view describing an action of the mammography apparatus according to the second embodiment.
Figure 9:
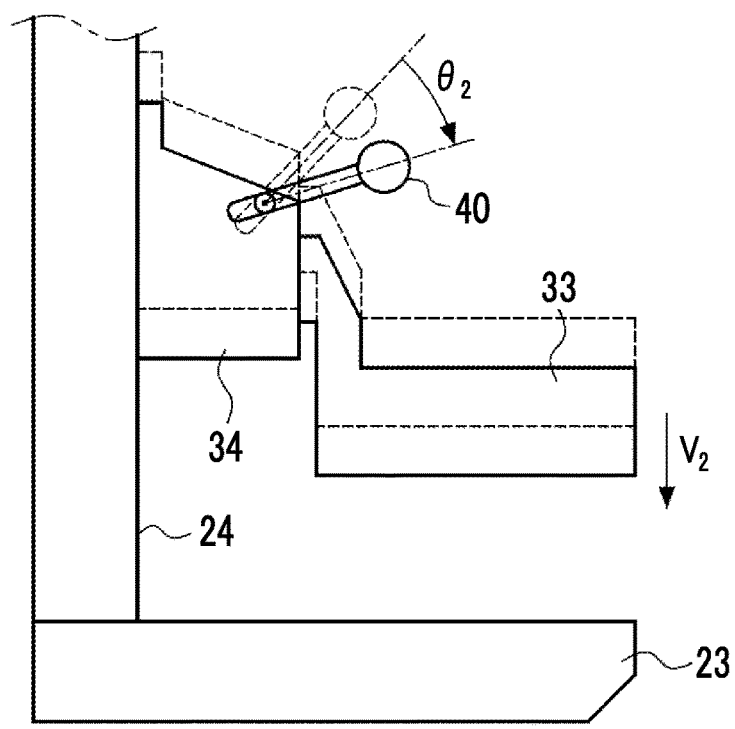

FIG. 9 describes an action of the mammography apparatus according to the second embodiment. FIG. 9 shows the change in the speed V in a case in which the angle θ of the operation portion 40 is increased. As shown in FIG. 9, in the present embodiment, in a case in which the angle θ of the operation portion 40 is increased from θ₁ to θ₂, the speed V of the compression plate 33 is increased from V₁ to V₂. FIG. 9 shows a case in which the operation portion 40 is displaced in the downward direction, but the same applies to a case in which the operation portion 40 is displaced in the upward direction.

In the present embodiment, the movement speed of the compression plate 33 is faster as the displacement amount of the operation portion 40 is larger, so that the operator can intuitively perform the operation.

Third Embodiment

Next, a mammography apparatus according to a third embodiment will be described. The third embodiment is different from the first embodiment in the functional configuration of the processor 60 and in that an encoder 57 is connected to the motor 54.

Figure 10:
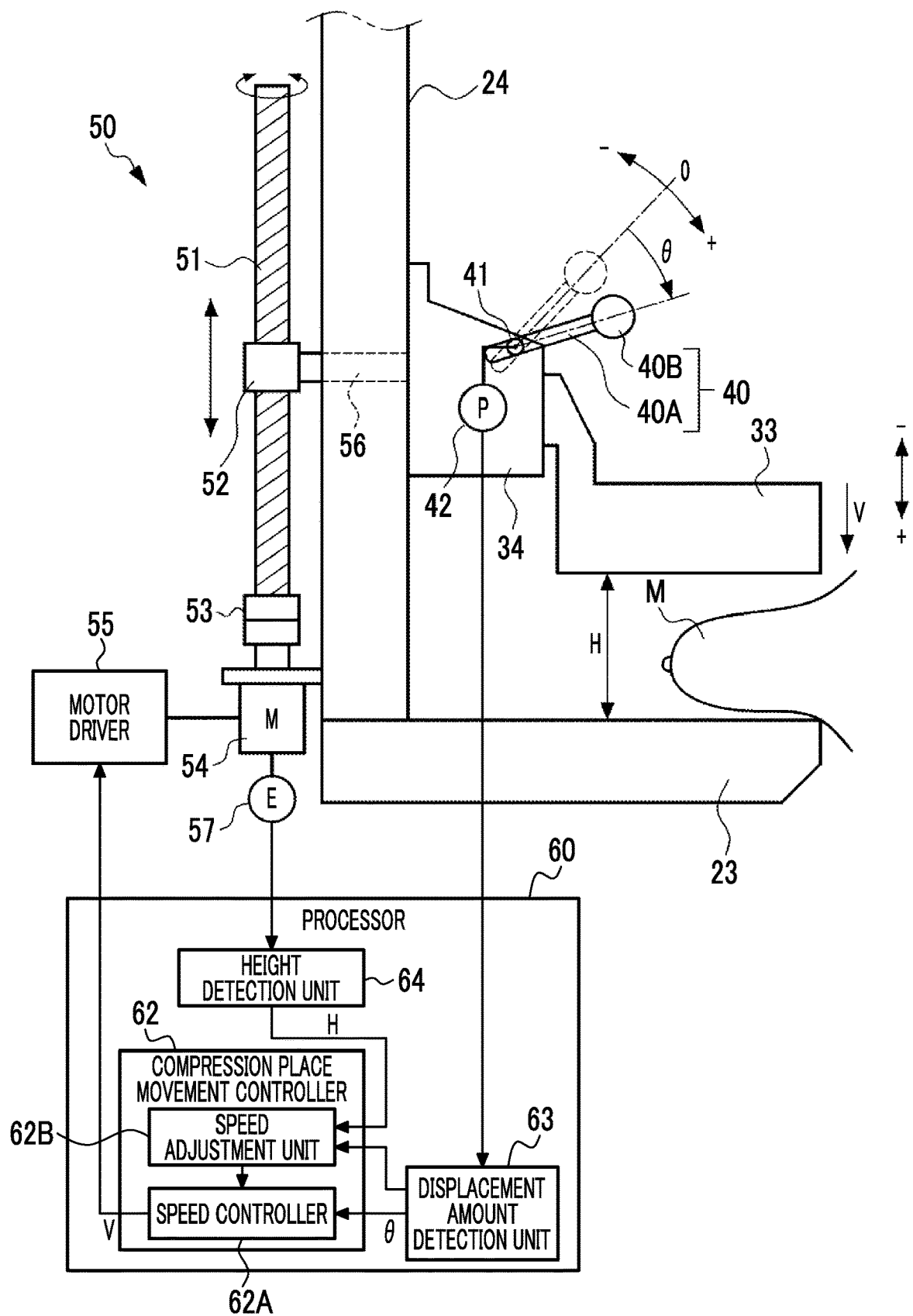
FIG. 10 is a view showing a configuration of a mammography apparatus according to a third embodiment.

FIG. 10 shows a configuration of the mammography apparatus according to the third embodiment. As shown in FIG. 10, in the present embodiment, the processor 60 includes the displacement amount detection unit 63, a height detection unit 64, and the compression plate movement controller 62. In addition, the compression plate movement controller 62 includes the speed controller 62A and a speed adjustment unit 62B. Further, in the present embodiment, the encoder 57 is connected to the motor 54.

The displacement amount detection unit 63 and the speed controller 62A have the same functions as the displacement amount detection unit 63 and the speed controller 62A described in the second embodiment. The displacement amount detection unit 63 detects the angle θ of the operation portion 40. The speed controller 62A obtains the speed V corresponding to the angle θ detected by the displacement amount detection unit 63, and controls the motor driver 55 such that the compression plate 33 is moved at the obtained speed V.

The encoder 57 converts a mechanical displacement amount of the rotation of the motor 54 into an electric signal and outputs the converted electric signal. The height detection unit 64 detects a height H of the compression plate 33 with respect to the imaging table 23 based on the output signal output from the encoder 57. The height H refers to an interval between the compression plate 33 and the imaging table 23. The height H of the compression plate 33 with respect to the imaging table 23 is higher as the interval between the compression plate 33 and the imaging table 23 is wider, and the height H of the compression plate 33 with respect to the imaging table 23 is lower as the interval therebetween is narrower.

Specifically, the output signal of the encoder 57 includes a pulse in response to the rotation of the motor 54. The height detection unit 64 counts the number of the pulses included in the output signal of the encoder 57, and converts the counted number of the pulses into a distance to obtain the height H. Note that it is also possible to use a potentiometer instead of the encoder 57.

The speed adjustment unit 62B adjusts the speed V of the compression plate 33 controlled by the speed controller 62A. In the present embodiment, the speed adjustment unit 62B adjusts an initial speed Vi of the compression plate 33 in response to the height H detected by the height detection unit 64 and the displacement direction of the compression plate 33. The initial speed Vi is the movement speed immediately after the start of movement of the compression plate 33, which is moved from a stationary state. After the start of movement of the compression plate 33, during a certain period of time, the speed adjustment unit 62B applies the initial speed Vi in response to the height H and the displacement direction of the compression plate 33 instead of the speed V obtained by the speed controller 62A. Note that the period of time during which the initial speed Vi is applied may be a fixed value, but may be the time from the start of movement of the compression plate 33 to the time when a movement amount reaches a defined value.

Figure 11:
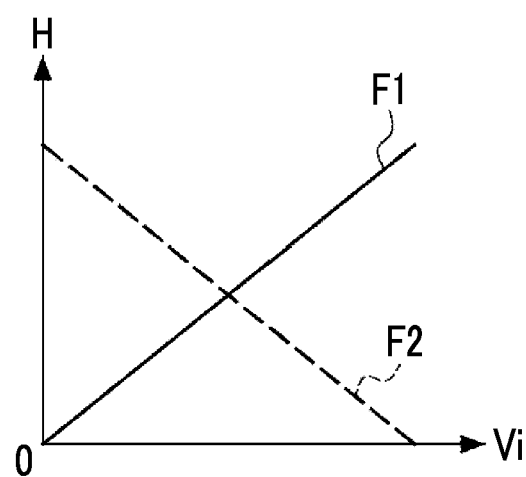
FIG. 11 is a graph showing an example of a relationship between a height and an initial speed.

The speed adjustment unit 62B decides the initial speed Vi, for example, based on a relationship between the height H and the initial speed Vi shown in FIG. 11. The speed adjustment unit 62B obtains the displacement direction of the compression plate 33 based on the angle θ as the displacement amount detected by the displacement amount detection unit 63.

In a case in which the displacement direction of the compression plate 33 is the downward direction, the speed adjustment unit 62B decides the initial speed Vi by using a first function F1. In addition, in a case in which the displacement direction of the compression plate 33 is the upward direction, the speed adjustment unit 62B decides the initial speed Vi by using a second function F2. In the first function F1, the initial speed Vi is faster as the height H is higher. On the contrary, in the second function F2, the initial speed Vi is faster as the height H is lower. In the present embodiment, the first function F1 and the second function F2 are linear functions, but the first function F1 and the second function F2 may be non-linear functions. In addition, the speed adjustment unit 62B may store information representing the first function F1 and the second function F2 as the LUT in the memory, and decide the initial speed Vi based on the LUT.

Figure 12:
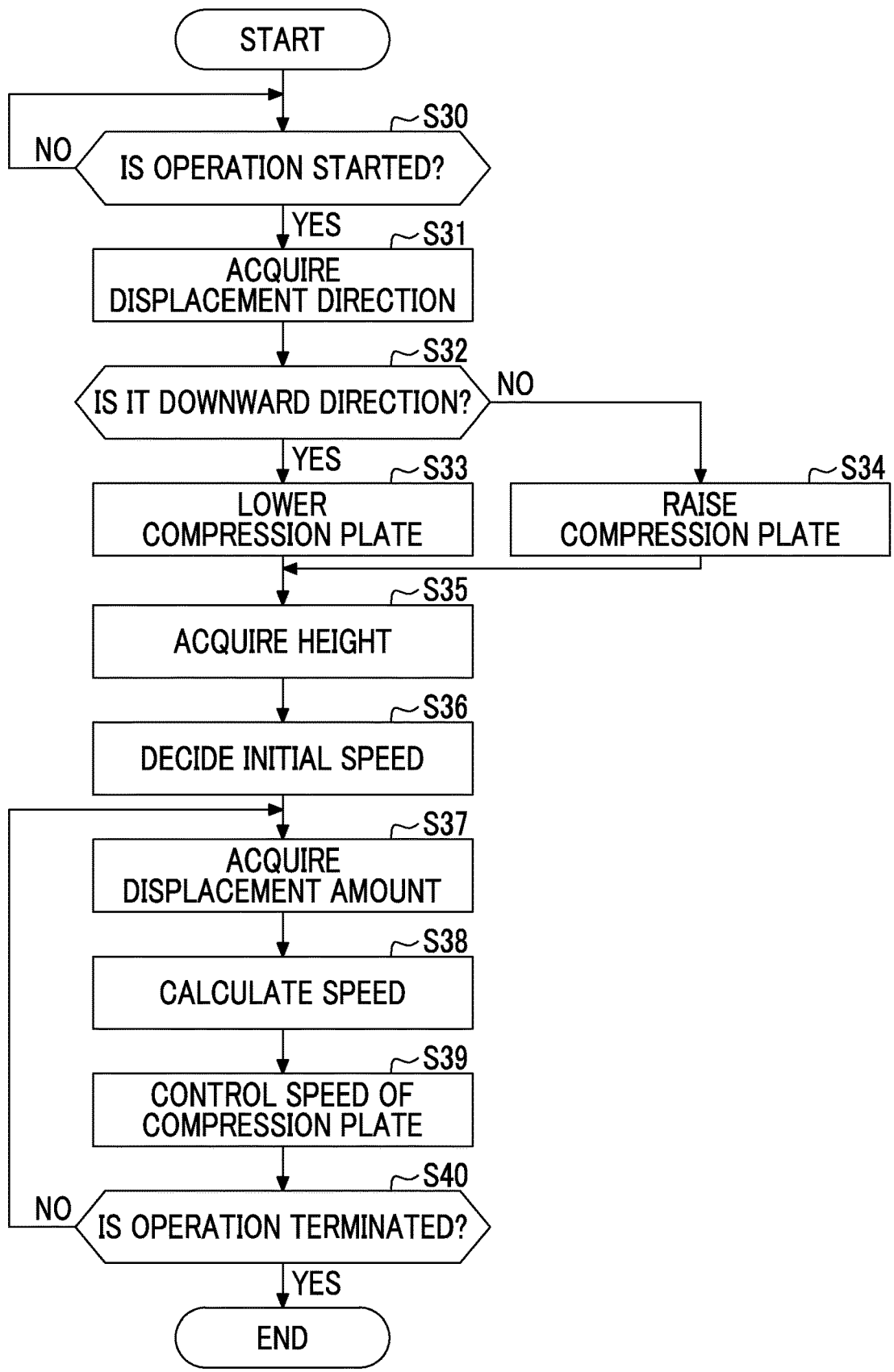
FIG. 12 is a flowchart showing an example of a movement control according to the third embodiment.

Next, an example of a movement control of the compression plate 33 according to the present embodiment will be described with reference to a flowchart shown in FIG. 12. Steps S30 to S34 shown in FIG. 12 are the same as steps S10 to S14 shown in FIG. 4, and thus the description thereof will be omitted.

After step S33 or step S34, the compression plate movement controller 62 acquires the height H detected by the height detection unit 64 (step S35). The speed adjustment unit 62B decides the initial speed Vi based on the height H acquired by the compression plate movement controller 62 (step S36). At this time, the speed adjustment unit 62B selects one of the first function F1 or the second function F2 based on the displacement direction detected by the displacement amount detection unit 63, and uses the selected function to decide the initial speed Vi corresponding to the height H.

Next, the compression plate movement controller 62 acquires the angle θ as the displacement amount detected by the displacement amount detection unit 63 (step S37). The speed controller 62A obtains the speed V based on the angle θ acquired by the compression plate movement controller 62 (step S38). Then, the speed controller 62A controls the drive mechanism 50 based on the initial speed Vi decided by the speed adjustment unit 62B and the obtained speed V (step S39). At this time, the speed controller 62A applies the initial speed Vi instead of the speed V for a certain period of time.

Thereafter, the compression plate movement controller 62 determines whether or not the operation of the operation portion 40 is terminated (step S40). In a case in which it is determined that the operation of the operation portion 40 is not terminated (step S40: NO), the compression plate movement controller 62 returns the process to step S37. In a case in which it is determined that the operation of the operation portion 40 is terminated (step S40: YES), the compression plate movement controller 62 terminates the process.

As described above, the acquisition of the height H (step S35) and the decision of the initial speed Vi (step S36) are executed only immediately after the start of the operation of the operation portion 40.

Figure 13:
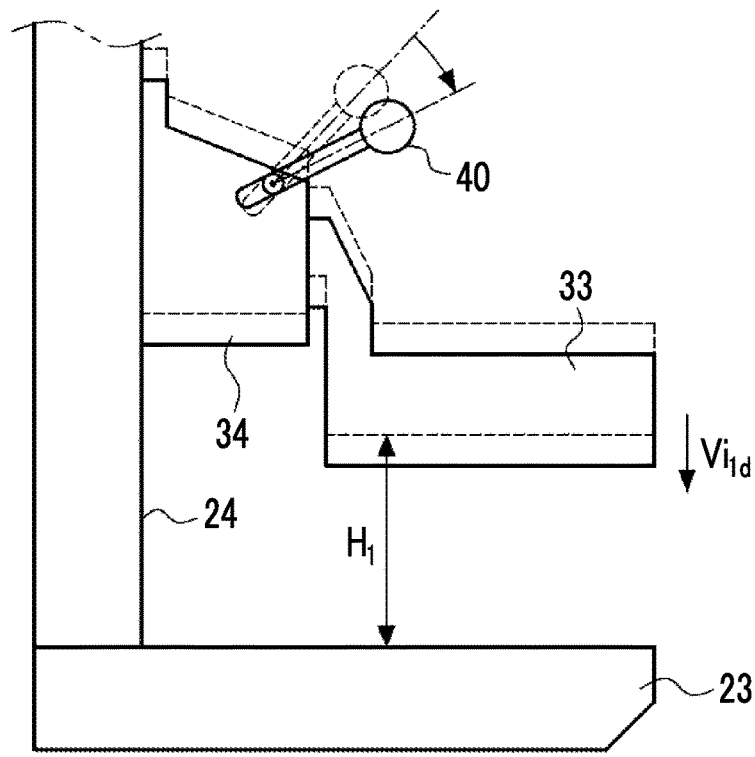
FIG. 13 is a view describing an action of the mammography apparatus according to the third embodiment.
Figure 13:
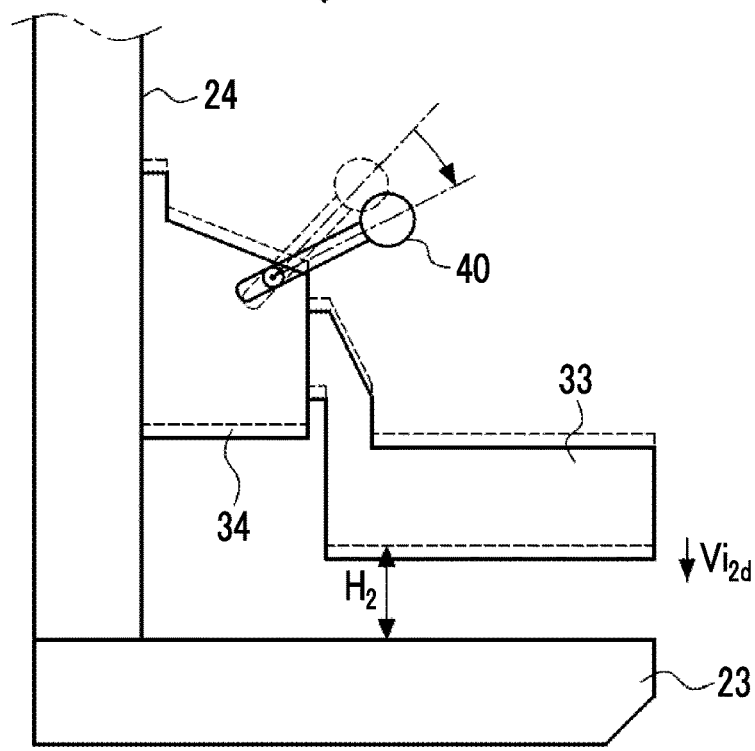
Figure 14:
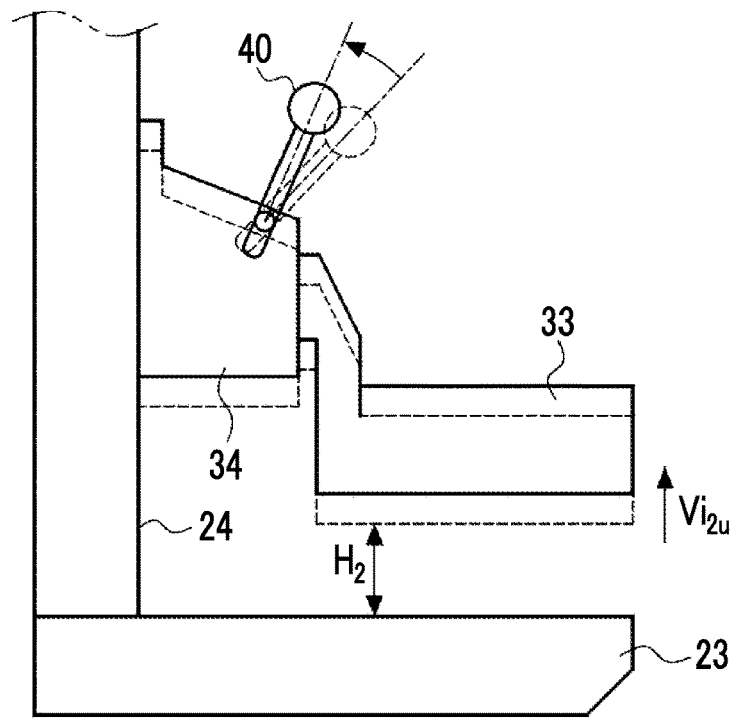
FIG. 14 is a view describing the action of the mammography apparatus according to the third embodiment.
Figure 14:
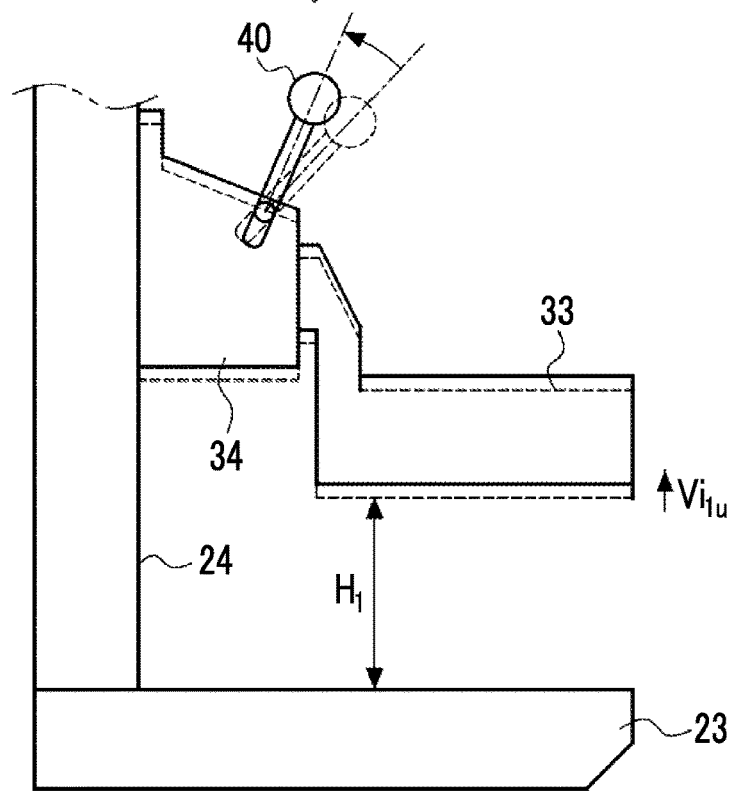

FIGS. 13 and 14 are views describing an action of the mammography apparatus according to the third embodiment. FIG. 13 shows the initial speed Vi in a case in which the compression plate 33 is lowered from two different heights H. An initial speed $Vi_{1d}$ of the compression plate 33 in a case in which the compression plate 33 is lowered from a state in which the compression plate 33 is positioned at a relatively high position (height $H_1$) is faster than an initial speed $Vi_{2d}$ of the compression plate 33 in a case in which the compression plate 33 is lowered from a state in which the compression plate 33 is positioned at a relatively low position (height $H_2$).

FIG. 14 shows the initial speed Vi in a case in which the compression plate 33 is raised from two different heights H. An initial speed $Vi_{2u}$ of the compression plate 33 in a case in which the compression plate 33 is raised from a state in which the compression plate 33 is positioned at a relatively low position (height $H_2$) is faster than an initial speed $Vi_{1u}$ of the compression plate 33 in a case in which the compression plate 33 is raised from a state in which the compression plate 33 is positioned at a relatively high position (height $H_1$).

In the present embodiment, the initial speed Vi is decreased in a case in which the compression plate 33 is moved from a position close to an upper limit or a lower limit of a movable range of the compression plate 33, so that the safety of the apparatus is improved.

Fourth Embodiment

Next, a mammography apparatus according to a fourth embodiment will be described. The fourth embodiment is different from the first embodiment only in the functional configuration of the processor 60.

Figure 15:
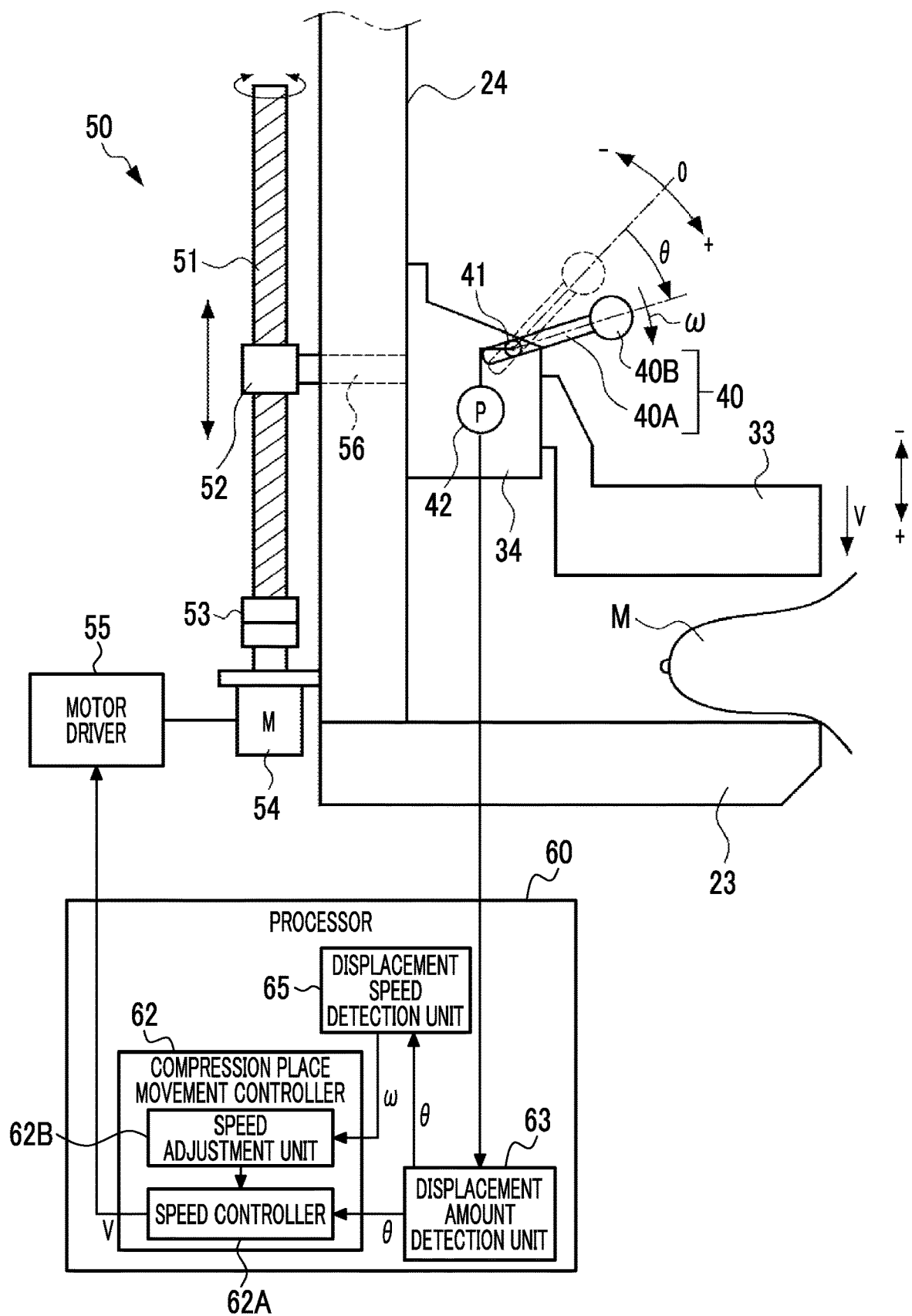
FIG. 15 is a view showing a configuration of a mammography apparatus according to a fourth embodiment.

FIG. 15 shows a configuration of the mammography apparatus according to the fourth embodiment. As shown in FIG. 15, in the present embodiment, the processor 60 includes the displacement amount detection unit 63, a displacement speed detection unit 65, and the compression plate movement controller 62. In addition, the compression plate movement controller 62 includes the speed controller 62A and the speed adjustment unit 62B.

The displacement amount detection unit 63 has the same function as the displacement amount detection unit 63 described in the second embodiment. The displacement amount detection unit 63 detects the angle θ of the operation portion 40.

The displacement speed detection unit 65 detects a displacement speed ω of the operation portion 40 by obtaining a rate of temporal change in the angle θ detected by the displacement amount detection unit 63. In the present embodiment, the displacement speed ω is an angular speed.

In the present embodiment, the speed adjustment unit 62B adjusts the speed V based on the displacement speed ω detected by the displacement speed detection unit 65. For example, the speed adjustment unit 62B adjusts the speed V by multiplying the speed V by a coefficient proportional to the magnitude of the displacement speed ω. That is, the speed adjustment unit 62B performs adjustment to set the speed V to be faster as the displacement speed ω is faster. In the present embodiment, the speed controller 62A controls the motor driver 55 such that the compression plate 33 is moved at the speed V adjusted by the speed adjustment unit 62B.

Figure 16:
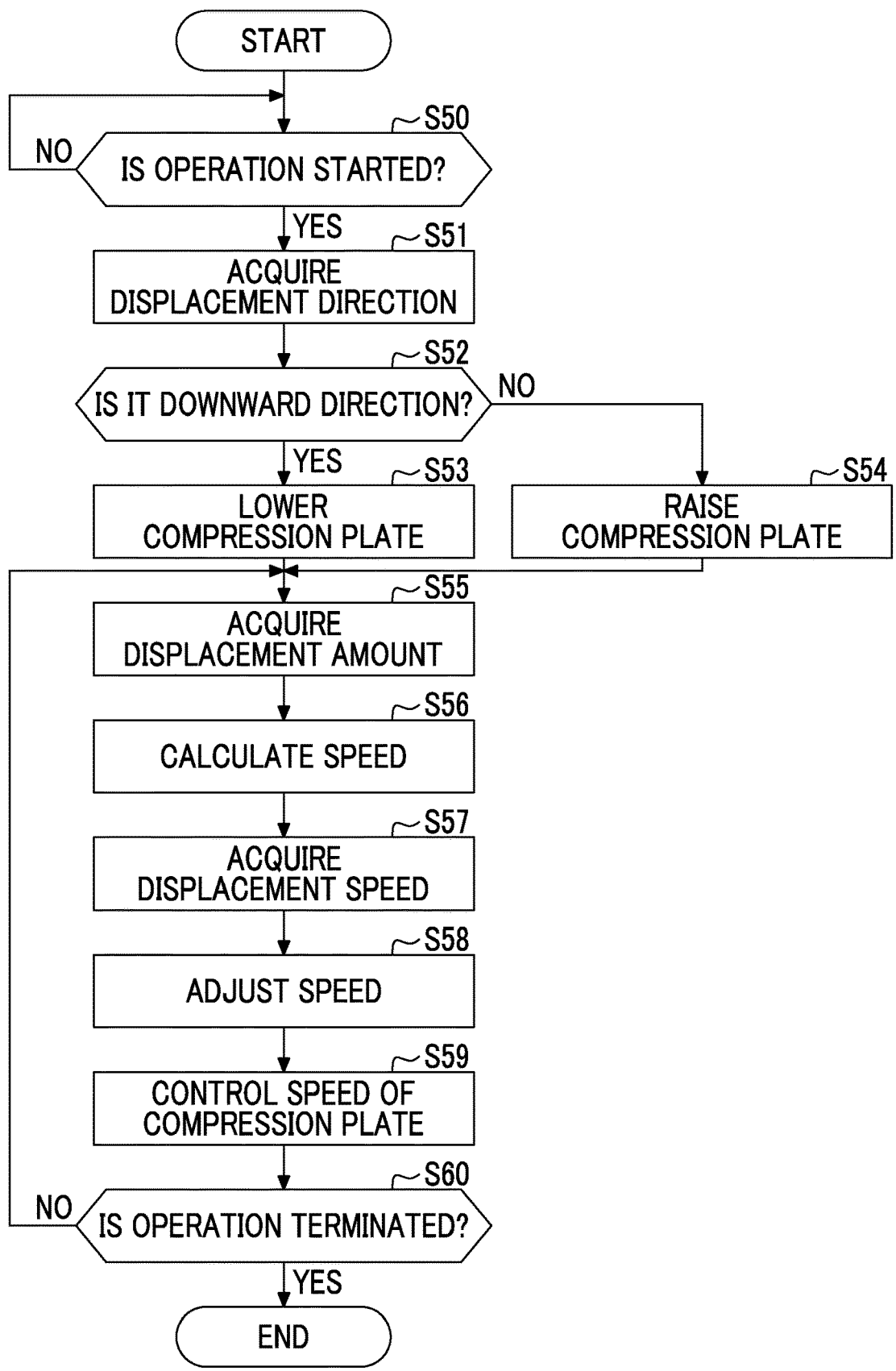
FIG. 16 is a flowchart showing an example of a movement control according to the fourth embodiment.

Next, an example of a movement control of the compression plate 33 according to the present embodiment will be described with reference to a flowchart shown in FIG. 16. Steps S50 to S54 shown in FIG. 16 are the same as steps S10 to S14 shown in FIG. 4, and thus the description thereof will be omitted.

After step S53 or step S54, the compression plate movement controller 62 acquires the angle θ as the displacement amount detected by the displacement amount detection unit 63 (step S55). The speed controller 62A obtains the speed V based on the angle θ acquired by the compression plate movement controller 62 (step S56).

Next, the compression plate movement controller 62 acquires the displacement speed ω detected by the displacement speed detection unit 65 (step S57). The speed adjustment unit 62B adjusts the speed V based on the displacement speed ω acquired by the compression plate movement controller 62 (step S58). Then, the speed controller 62A controls the drive mechanism 50 such that the compression plate 33 is moved at the adjusted speed V (step S59).

Thereafter, the compression plate movement controller 62 determines whether or not the operation of the operation portion 40 is terminated (step S60). In a case in which it is determined that the operation of the operation portion 40 is not terminated (step S60: NO), the compression plate movement controller 62 returns the process to step S55. In a case in which it is determined that the operation of the operation portion 40 is terminated (step S60: YES), the compression plate movement controller 62 terminates the process.

Figure 17:
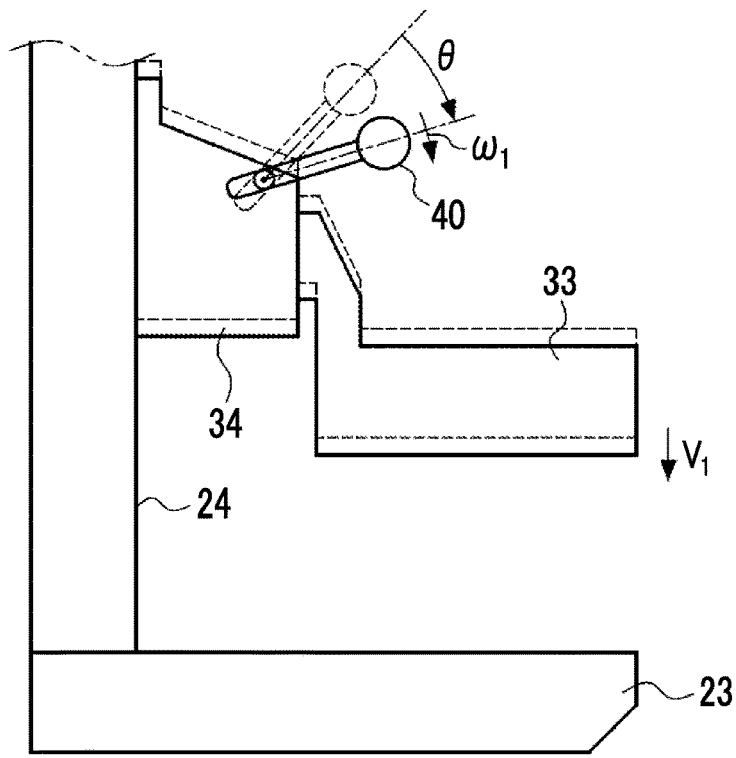
FIG. 17 is a view describing an action of the mammography apparatus according to the fourth embodiment.
Figure 17:
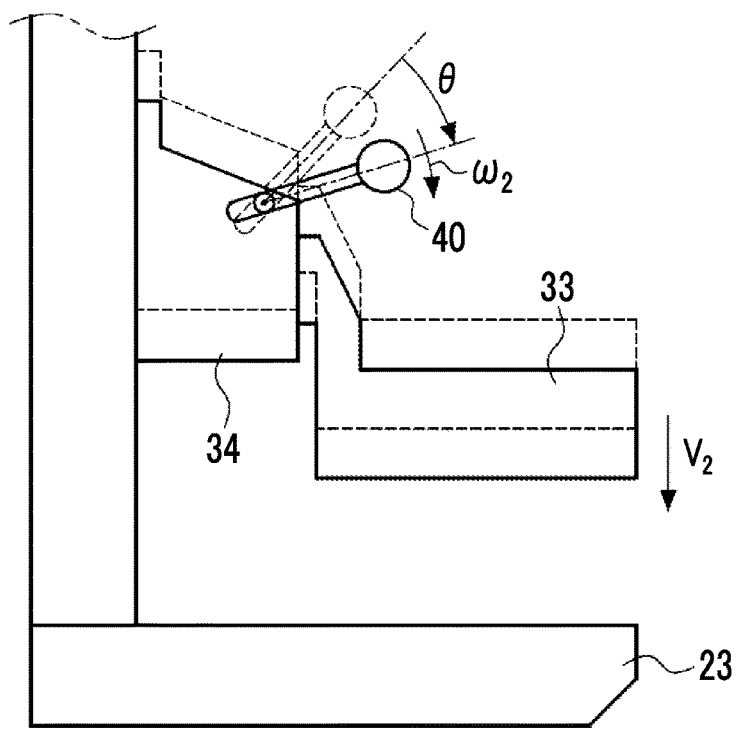

FIG. 17 describes an action of the mammography apparatus according to the fourth embodiment. FIG. 17 shows the speed V of the compression plate 33 in a case in which the angle θ of the operation portion 40 is the same and the displacement speed ω is different. Even in a case in which the angle θ is the same, in a case in which the displacement speed ω is relatively slow (displacement speed $ω_1$), the speed V is slow (speed $V_1$), and in a case in which the displacement speed ω is relatively fast (displacement speed $ω_2$), the speed V is fast (speed $V_2$). FIG. 17 shows a case in which the operation portion 40 is displaced in the downward direction, but the same applies to a case in which the operation portion 40 is displaced in the upward direction.

In the present embodiment, the movement speed of the compression plate 33 is faster as the operation portion 40 is displaced faster, so that the operator can intuitively perform the operation.

Fifth Embodiment

Next, a mammography apparatus according to a fifth embodiment will be described. The fifth embodiment is different from the first embodiment in the functional configuration of the processor 60 and in that a pressure sensor is provided on the compression plate 33.

Figure 18:
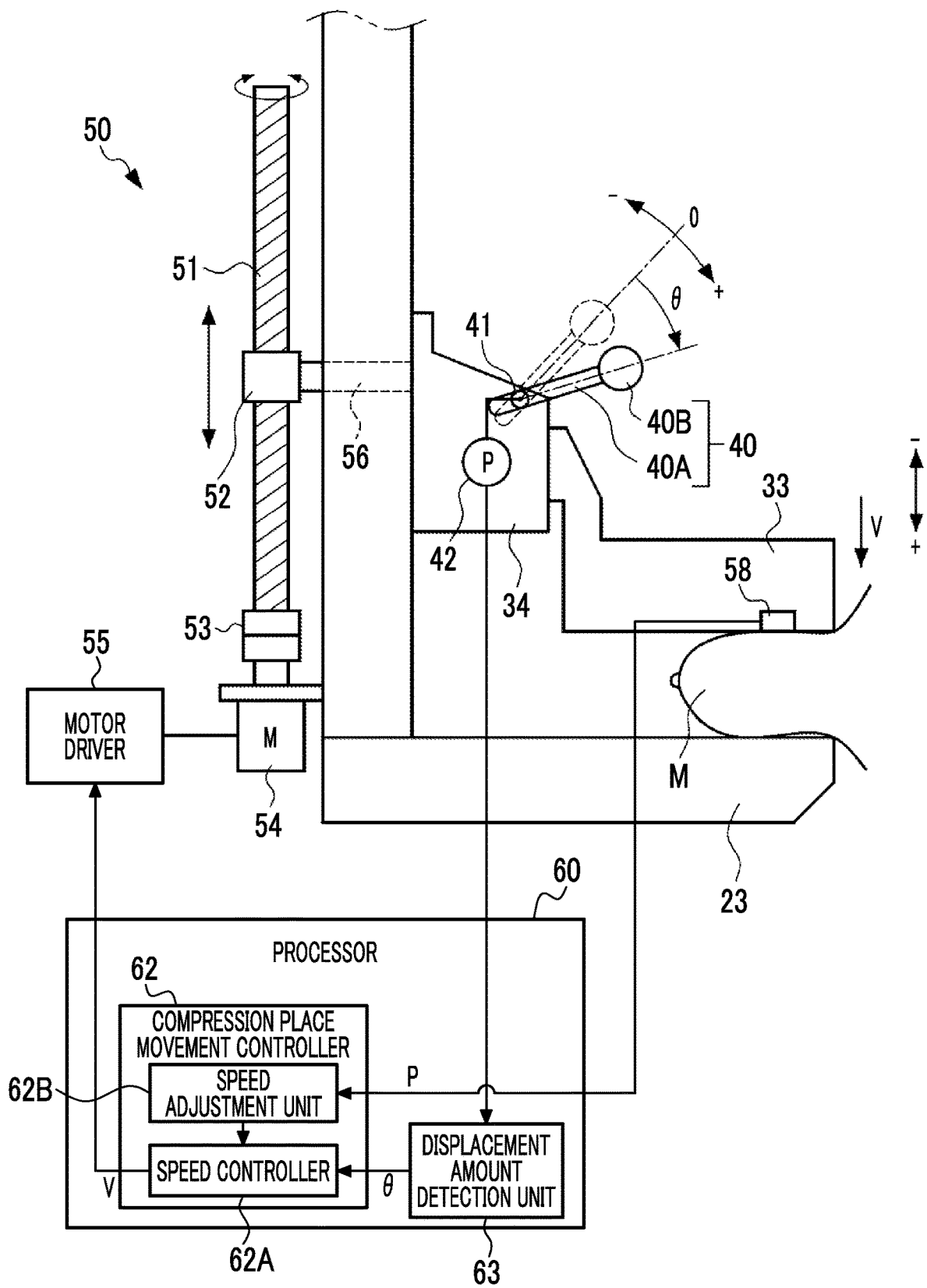
FIG. 18 is a view showing a configuration of a mammography apparatus according to a fifth embodiment.

FIG. 18 shows a configuration of the mammography apparatus according to the fifth embodiment. As shown in FIG. 18, in the present embodiment, the processor 60 includes the displacement amount detection unit 63 and the compression plate movement controller 62. In addition, the compression plate movement controller 62 includes the speed controller 62A and the speed adjustment unit 62B. Further, in the present embodiment, the compression plate 33 is provided with a pressure sensor 58 that detects a pressure P received from the breast M interposed between the imaging table 23 and the compression plate 33. As the pressure sensor 58, for example, a piezoelectric element is used. The pressure sensor 58 is an example of a "pressure detection unit" according to the technology of the present disclosure. Note that the pressure sensor 58 may be provided on the imaging table 23.

The displacement amount detection unit 63 has the same function as the displacement amount detection unit 63 described in the second embodiment. The displacement amount detection unit 63 detects the angle θ of the operation portion 40.

In the present embodiment, the speed adjustment unit 62B adjusts the speed V based on the pressure P detected by the pressure sensor 58. For example, the speed adjustment unit 62B adjusts the speed V by multiplying the speed V by a coefficient that is inversely proportional to the magnitude of the pressure P. That is, the speed adjustment unit 62B performs adjustment to set the speed V to be slower as the pressure P is larger. The speed controller 62A controls the motor driver 55 such that the compression plate 33 is moved at the speed V adjusted by the speed adjustment unit 62B. In the present embodiment, the rate of change in speed, which is a ratio of the change amount of the movement speed of the compression plate 33 to a unit displacement amount of the operation portion 40, is smaller as the pressure P is larger.

Figure 19:
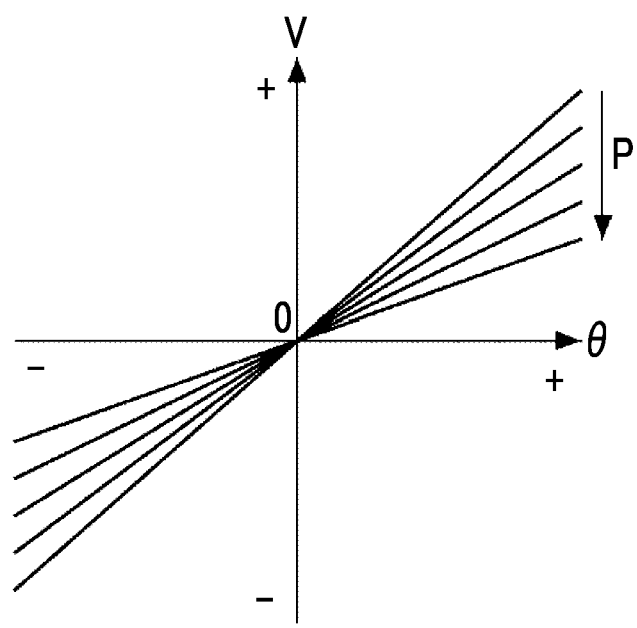
FIG. 19 is a graph showing a relationship between a rate of change in speed and a pressure.

FIG. 19 shows a relationship between the rate of change in speed and the pressure P. As shown in FIG. 19, in a case in which the relationship between the speed V and the angle θ is a proportional relationship, an inclination corresponding to the rate of change in speed is changed in response to the pressure P. The inclination is smaller as the pressure P is larger. Stated another way, in a case in which the angle θ of the operation portion 40 is fixed, the speed V is slower as the pressure P is larger.

Figure 20:
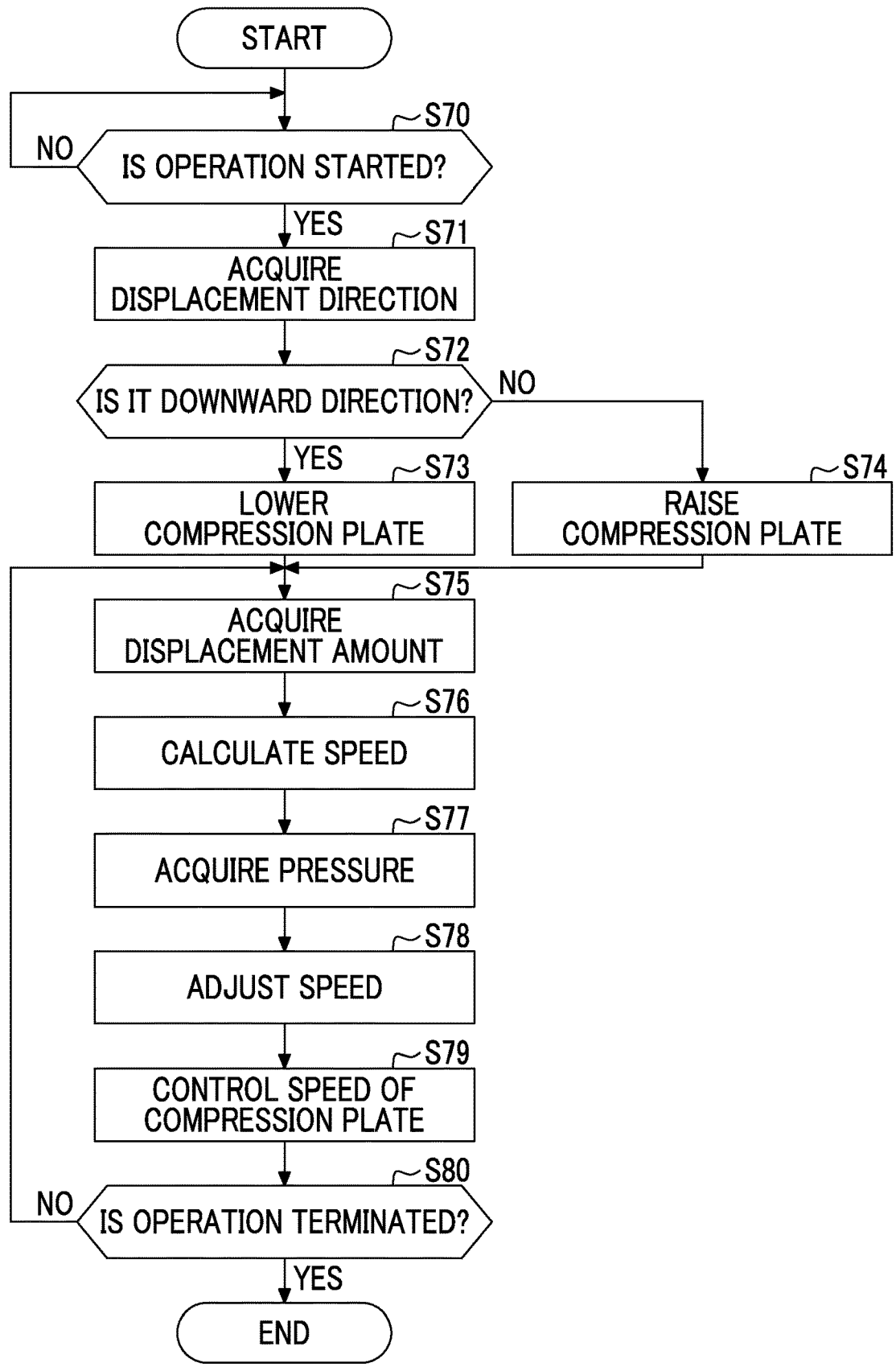
FIG. 20 is a flowchart showing an example of a movement control according to the fifth embodiment.

Next, an example of a movement control of the compression plate 33 according to the present embodiment will be described with reference to a flowchart shown in FIG. 20. Steps S70 to S74 shown in FIG. 20 are the same as steps S10 to S14 shown in FIG. 4, and thus the description thereof will be omitted.

After step S73 or step S74, the compression plate movement controller 62 acquires the angle θ as the displacement amount detected by the displacement amount detection unit 63 (step S75). The speed controller 62A obtains the speed V based on the angle θ acquired by the compression plate movement controller 62 (step S76).

Next, the compression plate movement controller 62 acquires the pressure P detected by the pressure sensor 58 (step S77). The speed adjustment unit 62B adjusts the speed V based on the pressure P acquired by the compression plate movement controller 62 (step S78). Then, the speed controller 62A controls the drive mechanism 50 such that the compression plate 33 is moved at the adjusted speed V (step S79).

Thereafter, the compression plate movement controller 62 determines whether or not the operation of the operation portion 40 is terminated (step S80). In a case in which it is determined that the operation of the operation portion 40 is not terminated (step S80: NO), the compression plate movement controller 62 returns the process to step S75. In a case in which it is determined that the operation of the operation portion 40 is terminated (step S80: YES), the compression plate movement controller 62 terminates the process.

Figure 21:
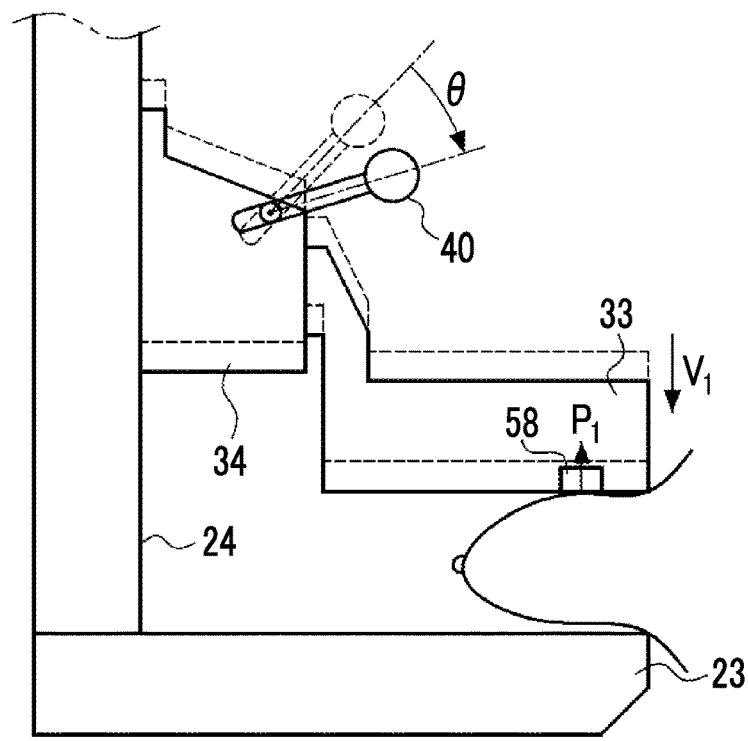
FIG. 21 is a view describing an action of the mammography apparatus according to the fifth embodiment.
Figure 21:
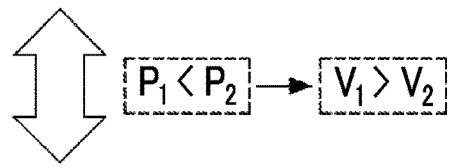
Figure 21:
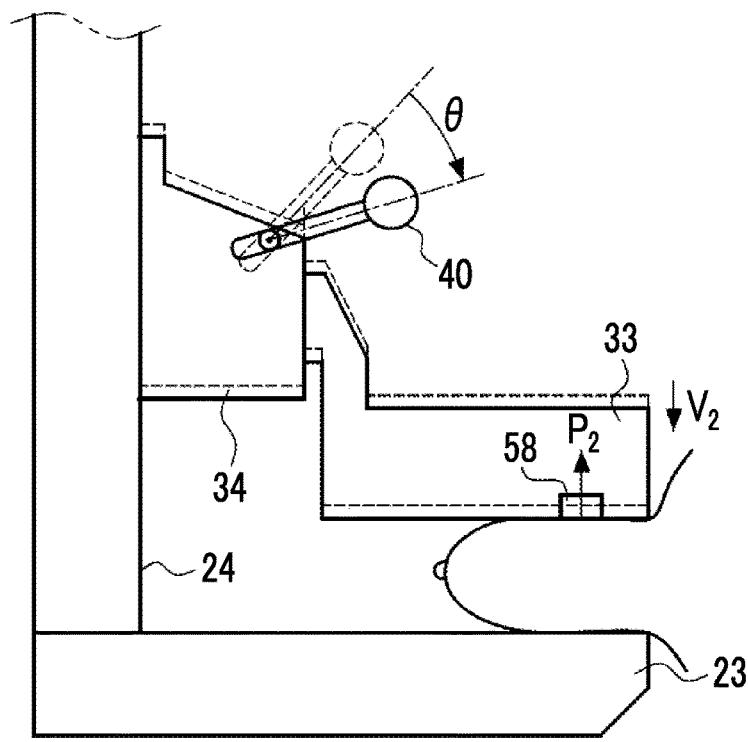

FIG. 21 describes an action of the mammography apparatus according to the fifth embodiment. FIG. 21 shows the speed V of the compression plate 33 in a case in which the angle θ of the operation portion 40 is the same and the pressure P is different. Even in a case in which the angle θ is the same, in a case in which the pressure P is relatively low (pressure $P_1$), the speed V is high (speed $V_1$), and in a case in which the pressure P is relatively high (pressure $P_2$), the speed V is slow (speed $V_2$).

In the present embodiment, the movement speed of the compression plate 33 is slower as the pressure of the breast M compressed by the compression plate 33 is larger, so that the safety of the apparatus is improved.

Figure 22:
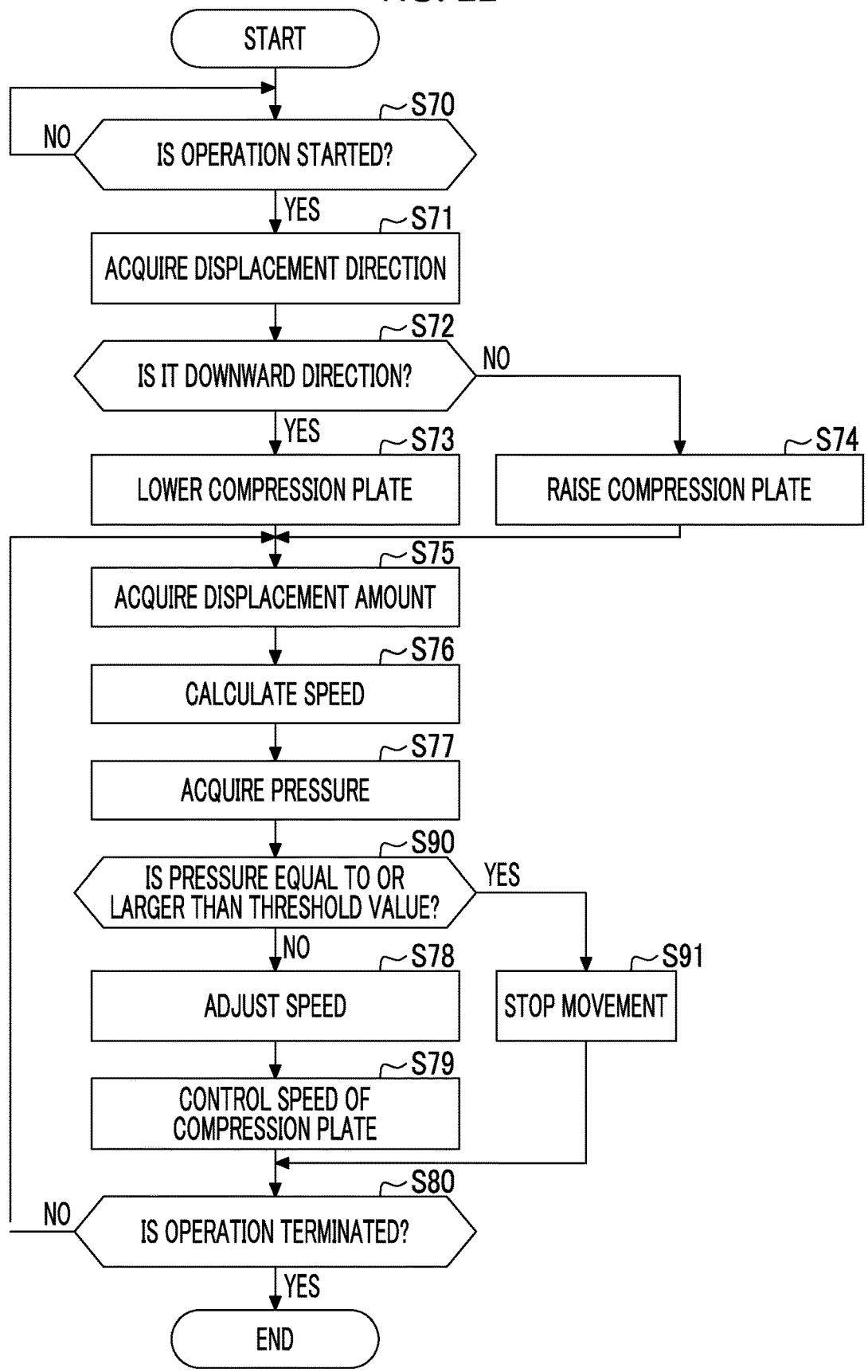
FIG. 22 is a flowchart describing a movement control according to a modification example of the fifth embodiment.

FIG. 22 is a flowchart describing a movement control of the compression plate 33 according to a modification example of the fifth embodiment. The flowchart shown in FIG. 22 is different from the flowchart shown in FIG. 20 in that steps S90 and S91 are added.

In step S90, the compression plate movement controller 62 determines whether or not the pressure P detected by the pressure sensor 58 is equal to or larger than a preset threshold value. In a case in which it is determined that the pressure P is not equal to or larger than the threshold value (step S90: NO), the compression plate movement controller 62 shifts the process to step S78. On the other hand, in a case in which it is determined that the pressure P is equal to or larger than the threshold value, the compression plate movement controller 62 stops the movement of the compression plate 33 (step S91). Thereafter, the compression plate movement controller 62 shifts the process to step S80.

According to the present modification example, even in a case in which the operation portion 40 is operated, the movement of the compression plate 33 is stopped in a case in which the pressure P is equal to or larger than the threshold value, and the height of the compression plate 33 is not changed, so that the safety is further improved.

Modification Example of Operation Portion

Various modification examples of the operation portion 40 are shown below.

First Modification Example

Figure 23:
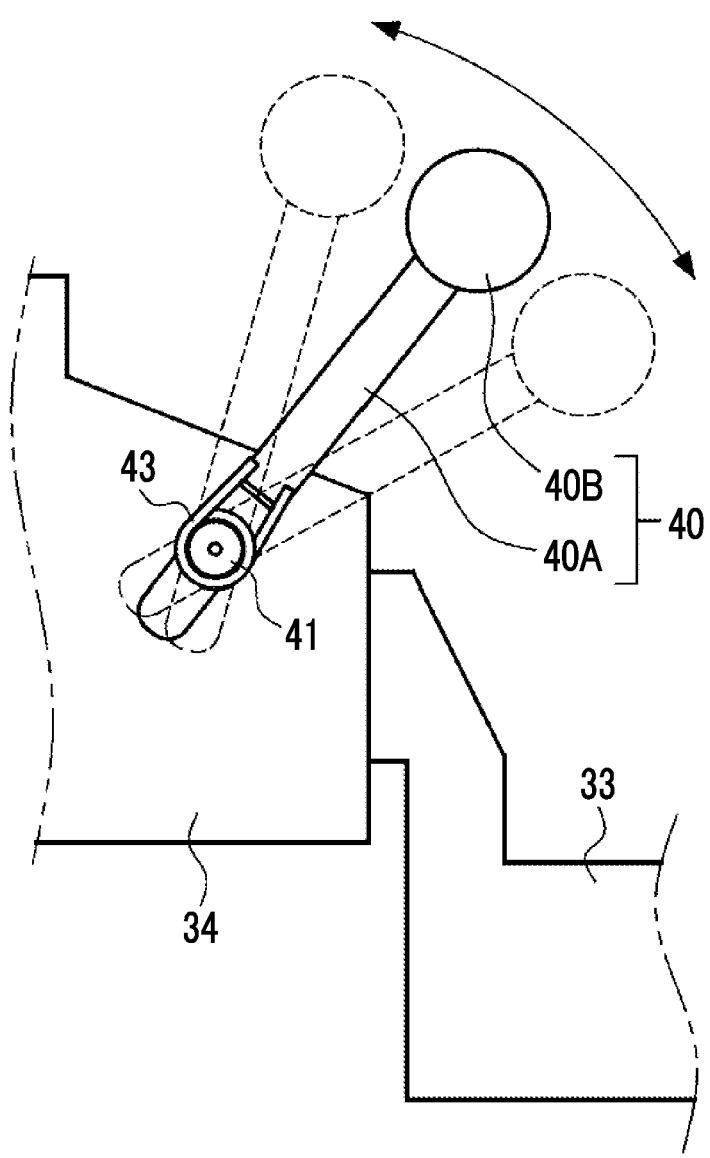
FIG. 23 is a view showing an operation portion according to a first modification example.

FIG. 23 shows the operation portion 40 according to a first modification example. In the present modification example, a coil spring 43 is attached to the rotation shaft 41 of the operation portion 40. The coil spring 43 is a biasing member that biases the operation portion 40 in a direction toward the neutral position shown by the solid line. Therefore, in a case in which the operation portion 40 is not operated, a posture of the operation portion 40 is maintained in the neutral position by the coil spring 43.

The coil spring 43 increases a load for operating the operation portion 40. That is, the coil spring 43 functions as a load increasing unit for operating the operation portion 40. The load is larger as the displacement amount of the operation portion 40 is larger.

Figure 24:
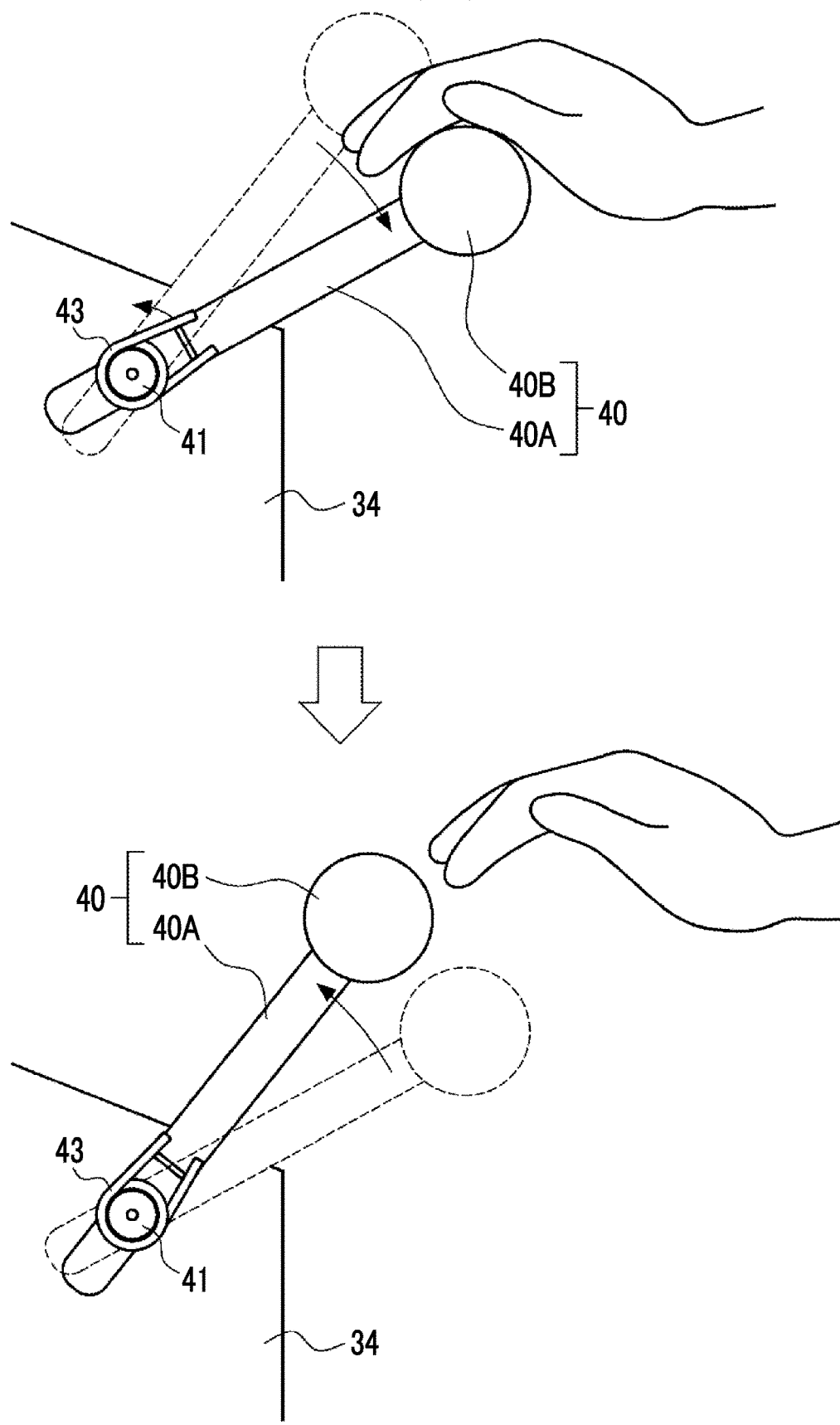
FIG. 24 is a view describing an action of a load increasing unit.

FIG. 24 describes an action of the load increasing unit. As shown in FIG. 24, in a case in which the operator manually displaces the operation portion 40 in the downward direction, the load increasing unit generates the load in a direction of returning the operation portion 40 to the neutral position. In a case in which the hand is released from the operation portion 40, the operation portion 40 is returned to the neutral position.

By biasing the operation portion 40 to the neutral position, the operation portion 40 can be easily displaced in the vertical direction with the neutral position as a reference. In addition, the operator can intuitively recognize the displacement amount of the operation portion 40 depending on the magnitude of the load.

Note that in the present modification example, a coil spring is used as the load increasing unit, but the load increasing unit is not limited to the coil spring, and various springs can be used. In addition, the load increasing unit is not limited to the spring, and a gear or the like may be used. In addition, as the load increasing unit, a frictional force generation mechanism in which an electric actuator and a friction plate are combined may be used. The frictional force generation mechanism increases the frictional force in a direction opposite to the operation direction of the operation portion 40 in response to the displacement amount of the operation portion 40, for example. It is needless to say that in a case in which the spring is used as in the present example, a configuration is simple as compared with a case in which such a frictional force generation mechanism is used.

Second Modification Example

Figure 25:
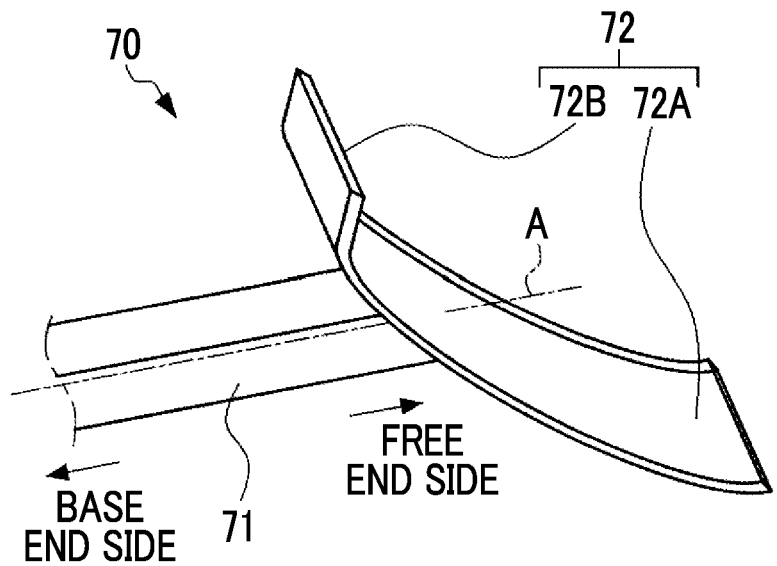
FIG. 25 is a perspective view showing an operation portion according to a second modification example.
Figure 26:
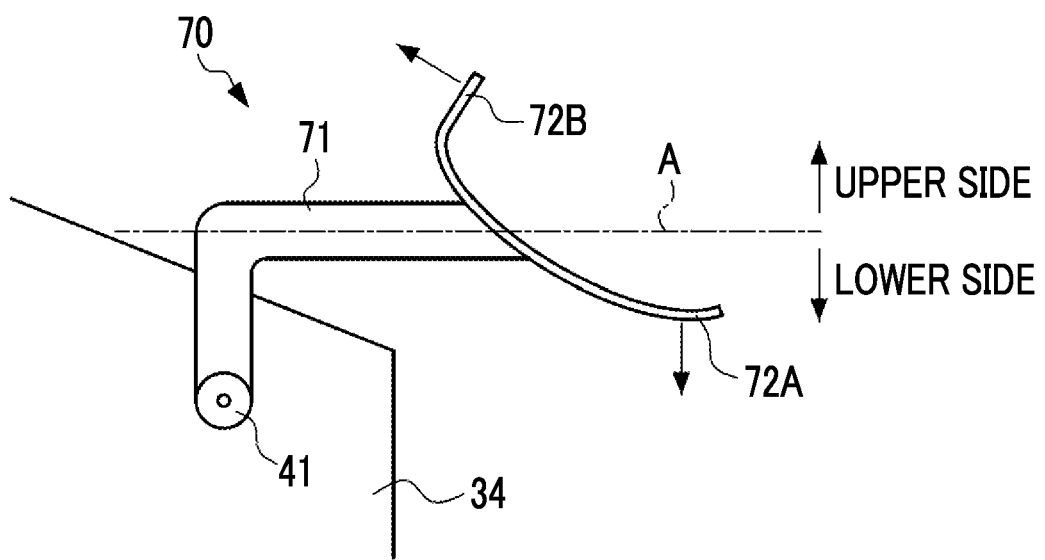
FIG. 26 is a side view showing the operation portion according to the second modification example.

FIGS. 25 and 26 show an operation portion 70 according to a second modification example. The operation portion 70 includes a main shaft portion 71 extending from the base end side to the free end side, and a protruding portion 72 provided at the free end of the main shaft portion 71. The protruding portion 72 includes a first protruding portion 72A and a second protruding portion 72B. The first protruding portion 72A and the second protruding portion 72B are integrally formed. The protruding portion 72 intersects an axis A of the main shaft portion 71 and is curved in a convex shape toward the base end side of the main shaft portion 71.

The first protruding portion 72A protrudes to a lower side with the axis A of the main shaft portion 71 as a reference. The second protruding portion 72B protrudes to an upper side with the axis A of the main shaft portion 71 as a reference. The axis A represents an axial direction of the main shaft portion 71.

Figure 27:
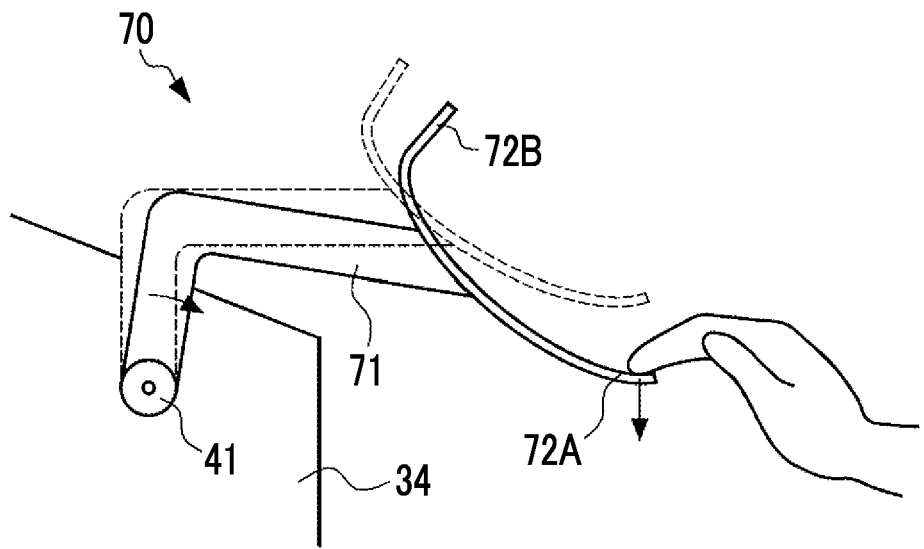
FIG. 27 is a view showing an aspect in which the operation portion according to the second modification example is displaced in a downward direction.

FIG. 27 shows an aspect in which the operator displaces the operation portion 70 in the downward direction. As shown in FIG. 27, the operator can rotate the operation portion 70 in a direction in which the compression plate 33 is lowered by pressing the first protruding portion 72A in the downward direction, for example. In addition, the operator can also rotate the operation portion 70 in the direction in which the compression plate 33 is lowered by pressing the second protruding portion 72B in the downward direction.

Figure 28:
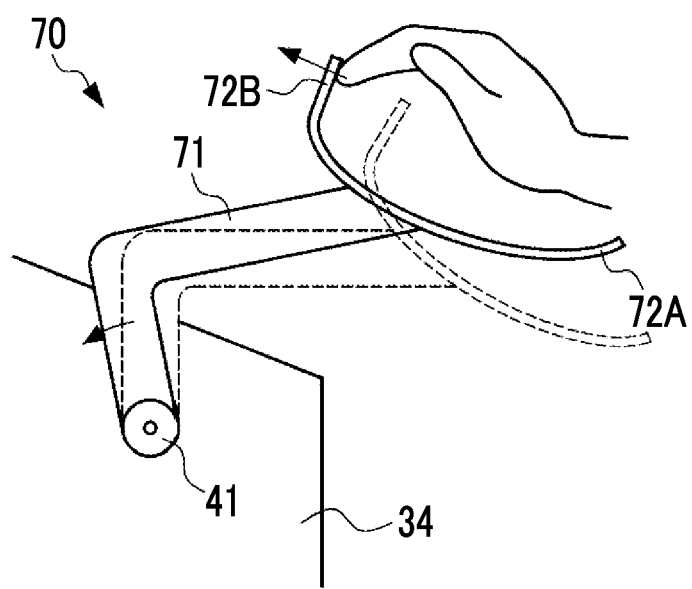
FIG. 28 is a view showing an aspect in which the operation portion according to the second modification example is displaced in an upward direction.

FIG. 28 shows an aspect in which the operator displaces the operation portion 70 in the upward direction. As shown in FIG. 28, for example, the operator can rotate the operation portion 70 in a direction in which the compression plate 33 is raised by pressing the second protruding portion 72B to the base end side of the main shaft portion 71. In addition, the operator can also rotate the operation portion 70 in the direction in which the compression plate 33 raised by pressing the first protruding portion 72A in the upward direction.

Third Modification Example

Figure 29:
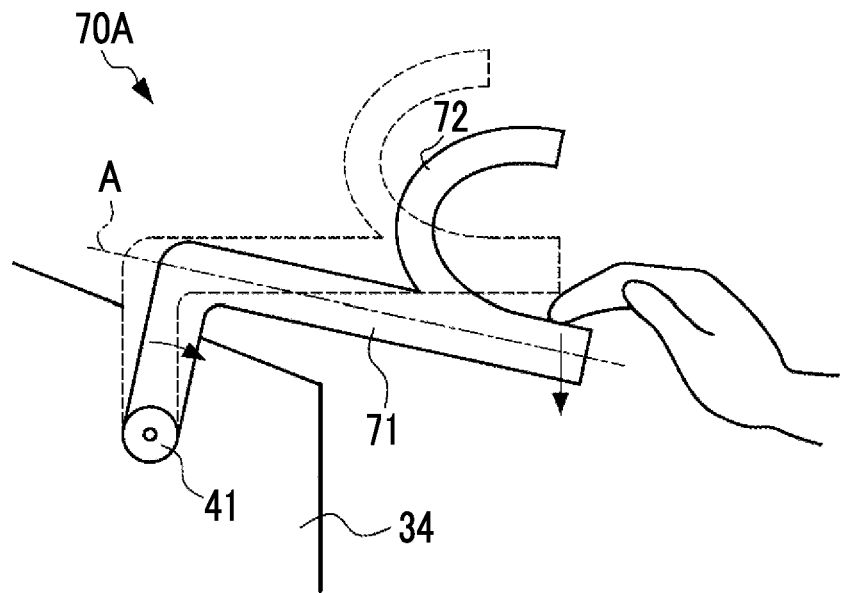
FIG. 29 is a view showing an aspect in which an operation portion according to a third modification example is displaced in the downward direction.
Figure 30:
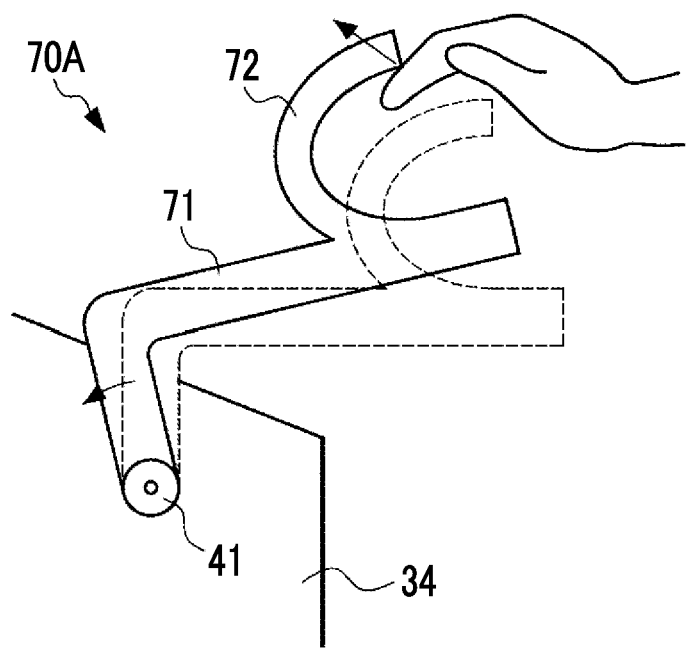
FIG. 30 is a view showing an aspect in which the operation portion according to the third modification example is displaced in the upward direction.

FIGS. 29 and 30 show an operation portion 70A according to a third modification example. The operation portion 70A includes the main shaft portion 71 extending from the base end side to the free end side, and the protruding portion 72 provided at the free end of the main shaft portion 71. In the present modification example, the protruding portion 72 has a hook shape that is curved in a convex toward the body portion 24 (see FIG. 3) side of the mammography apparatus 10 (that is, the base end side of the main shaft portion 71), and is joined to the main shaft portion 71. The protruding portion 72 is provided on the upper side of the main shaft portion 71 with the axis A as a reference.

As shown in FIG. 29, the operator can rotate the operation portion 70A in the direction in which the compression plate 33 is lowered by pressing a lower part of the protruding portion 72 in the downward direction, for example. In addition, as shown in FIG. 30, the operator can rotate the operation portion 70A in the direction in which the compression plate 33 is raised by pressing an upper part of the protruding portion 72 to the base end side of the main shaft portion 71, for example.

Fourth Modification Example

Figure 31:
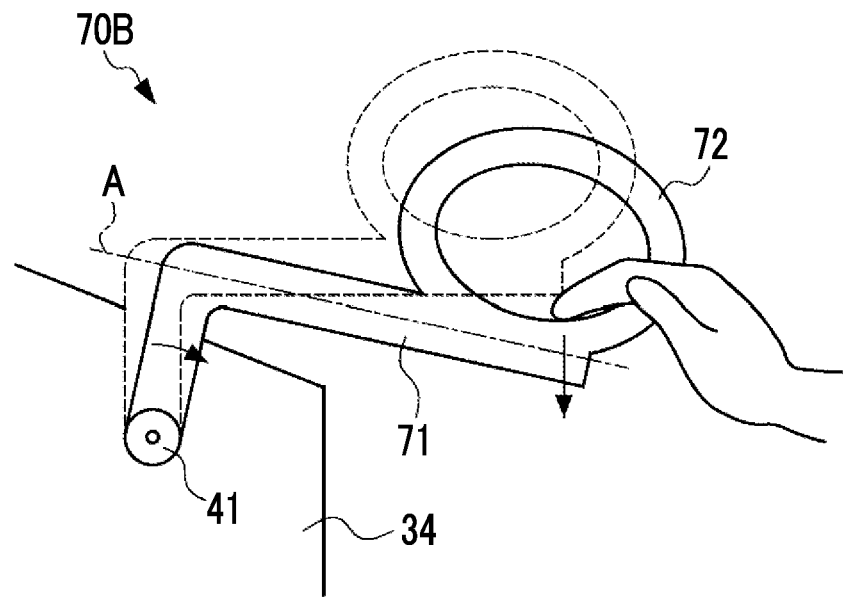
FIG. 31 is a view showing an aspect in which an operation portion according to a fourth modification example is displaced in the downward direction.
Figure 32:
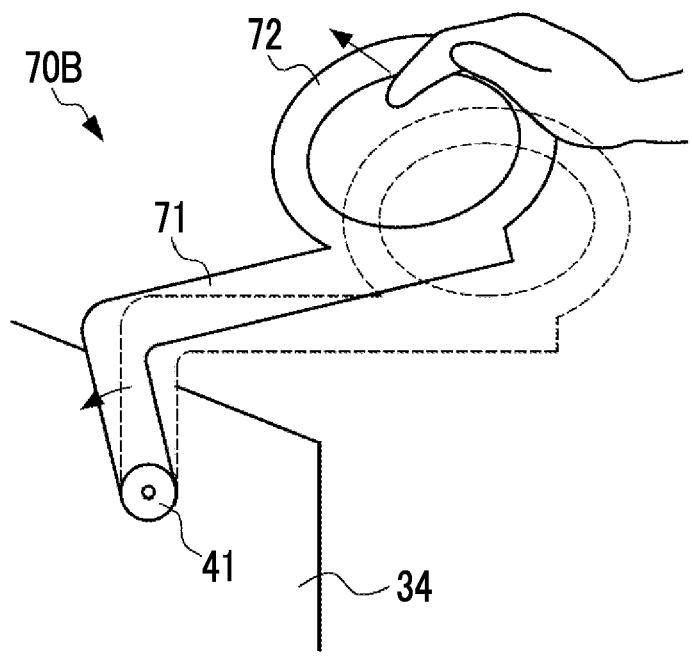
FIG. 32 is a view showing an aspect in which the operation portion according to the fourth modification example is displaced in the upward direction.

FIGS. 31 and 32 show an operation portion 70B according to a fourth modification example. The operation portion 70B includes the main shaft portion 71 extending from the base end side to the free end side, and the protruding portion 72 provided at the free end of the main shaft portion 71. In the present modification example, the protruding portion 72 has a ring shape. The protruding portion 72 has an elliptical shape in which a long axis is parallel to the axis A of the main shaft portion 71, for example. The protruding portion 72 is provided on the upper side of the main shaft portion 71 with the axis A as a reference.

As shown in FIG. 31, the operator can rotate the operation portion 70B in the direction in which the compression plate 33 is lowered by pressing the lower part of the protruding portion 72 in the downward direction, for example. In addition, as shown in FIG. 32, the operator can rotate the operation portion 70B in the direction in which the compression plate 33 is raised by pressing the upper part of the protruding portion 72 to the base end side of the main shaft portion 71, for example.

Note that in the third modification example and the fourth modification example, the protruding portion 72 is provided on the upper side of the main shaft portion 71 with the axis A as a reference, but may be provided on the lower side with the axis A as a reference.

Action and Effect of Protruding Portion

Next, an action and an effect of the protruding portion 72 described in the second to fourth modification examples will be described in detail. First, a situation is considered in which the protruding portion 72 is positioned on the upper side of the main shaft portion 71 and the operator extends the hand to the operation portion 70 from the free end side to perform the operation. Since both the main shaft portion 71 and the protruding portion 72 are a part of the operation portion 70, it is possible to rotate the operation portion 70 about the fulcrum on the base end side by pressing any one of the main shaft portion 71 or the protruding portion 72.

Then, in a case in which the operator disposes the hand from the free end side to the upper side of the main shaft portion 71 and presses the operation portion 70 in the downward direction from the upper side, the operation portion rotates in a first direction about the fulcrum. Similarly, in a case in which the operator disposes the hand from the free end side to the upper side of the main shaft portion 71 and presses the protruding portion 72 that protrudes to the upper side of the main shaft portion 71 to the base end side, it is possible to rotate the protruding portion 72 about the fulcrum. However, in this case, depending on a positional relationship between the protruding portion 72 and the fulcrum, it is possible to rotate a lever in a second direction opposite to the first direction by pressing the protruding portion 72.

Stated another way, by providing the protruding portion 72 that protrudes to the upper side of the main shaft portion 71, the operator can generate rotation moment with respect to the operation portion in a direction opposite to that of a case in which the operation portion is pressed in the downward direction from the upper side without changing a position of the hand disposed on the upper side of the main shaft portion. The same effect can be obtained even in a case in which the protruding portion 72 is provided on the lower side of the main shaft portion 71 depending on the positional relationship with the fulcrum.

As a comparative example, it is assumed that the operation portion is configured by only the main shaft portion 71 without providing the protruding portion 72. In the comparative example, in a case in which the operation portion rotates in the first direction, the operator can dispose the hand on the upper side of the main shaft portion 71 and press the upper side of the main shaft portion 71 in the downward direction to rotate the operation portion in the first direction. On the other hand, in a case in which the operation portion rotates in the second direction, the operator can dispose the hand on the lower side of the main shaft portion 71 and press the lower side of the main shaft portion 71 in the upward direction to rotate the operation portion in the second direction. However, in the comparative example, in a case in which the operator intends to change the rotation direction of the operation portion, it is necessary to change the position of the hand disposed on one of the upper side or the lower side of the main shaft portion 71.

Therefore, by providing the protruding portion 72 on the main shaft portion 71 as described above, even in a case in which the operator cannot grip the operation portion 70 from both sides of the upper side and the lower side, the operator can rotate the operation portion 70 any one direction of the first direction or the second direction only by the pressing operation without changing the position of the hand disposed one of the upper side or the lower side of the main shaft portion 71 to the opposite side. As described above, by providing the protruding portion 72 on the main shaft portion 71, the operability of the operation portion 70 is improved.

Since the operator of the mammography apparatus 10 is often restricted in the movement of the hand due to the positioning of the breast of the subject, a work such as gripping the operation portion 70 or changing the position of the hand between the upper side and the lower side across the main shaft portion 71 is difficult.

The effect of improving the operability of the operation portion 70 obtained by providing the protruding portion 72 on the main shaft portion 71 is significantly effective for the operator of the mammography apparatus 10 of which the movement of the hand is restricted. Further, the operation portion 70 is displaced along the vertical direction, which is the movement direction of the compression plate 33. In such an operation portion 70, it is significantly effective to improve the operability in the two directions of the upward direction and the downward direction by providing the protruding portion 72.

Action and Effect of Providing Operation Portion on Movable Portion

In the embodiments described above and each modification example, the operation portion is provided on the movable portion. Therefore, the operation portion is moved together with the movable portion. An action and an effect of providing the operation portion on the movable portion will be described.

Figure 33:
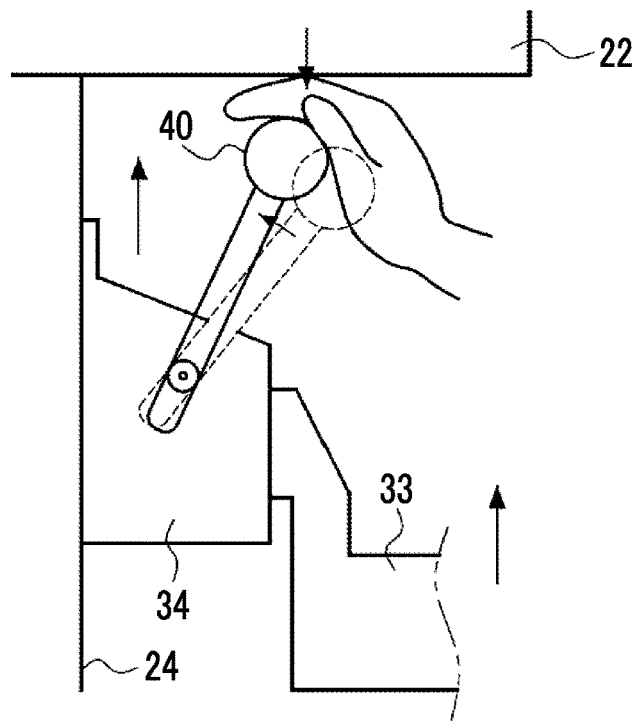
FIG. 33 is a view describing an action and an effect of providing the operation portion on a movable portion.
Figure 33:
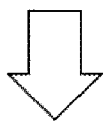
Figure 33:
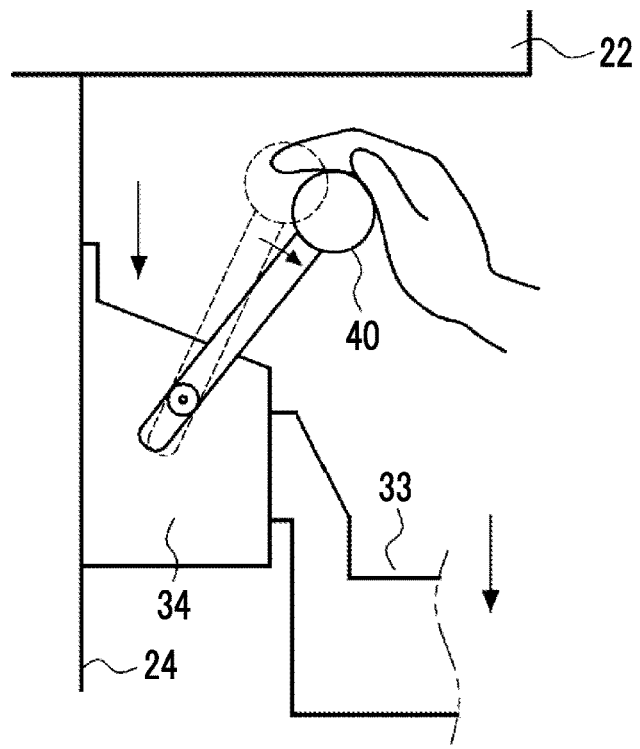

As shown in FIG. 33, in a case in which the operator grips the operation portion 40 by the hand and displaces the operation portion 40 in the upward direction, the operation portion 40 is raised together with the movable portion 34. In a case in which the movable portion 34 continues to be raised while the operator grips the operation portion 40 by the hand, there is a possibility that the hand comes into contact with the radiation source housing portion 22 provided above the body portion 24, and the hand is interposed between the operation portion 40 and the radiation source housing portion 22.

However, in a case in which the hand of the operator who grips the operation portion 40 comes into contact with the radiation source housing portion 22 while the movable portion 34 is raised, force acts in the downward direction from the radiation source housing portion 22, so that the operation portion 40 is displaced in the downward direction. As a result, the movable portion 34 is lowered, so that the contact between the hand of the operator and the radiation source housing portion 22 is released. As described above, even in a case in which the hand of the operator comes into contact with the radiation source housing portion 22, the contact is released in a short time, and the safety is improved.

As described above, by providing the operation portion 40 on the movable portion 34 and setting the displacement direction of the operation portion 40 and the movable portion 34 in the same direction, the safety is improved as well as the operability of the compression plate 33 is improved.

Attachment Position of Operation Portion

In the embodiments described above and each modification example, the operation portion is provided on the movable portion, but the operation portion may be provided in a place other than the movable portion.

Figure 34:
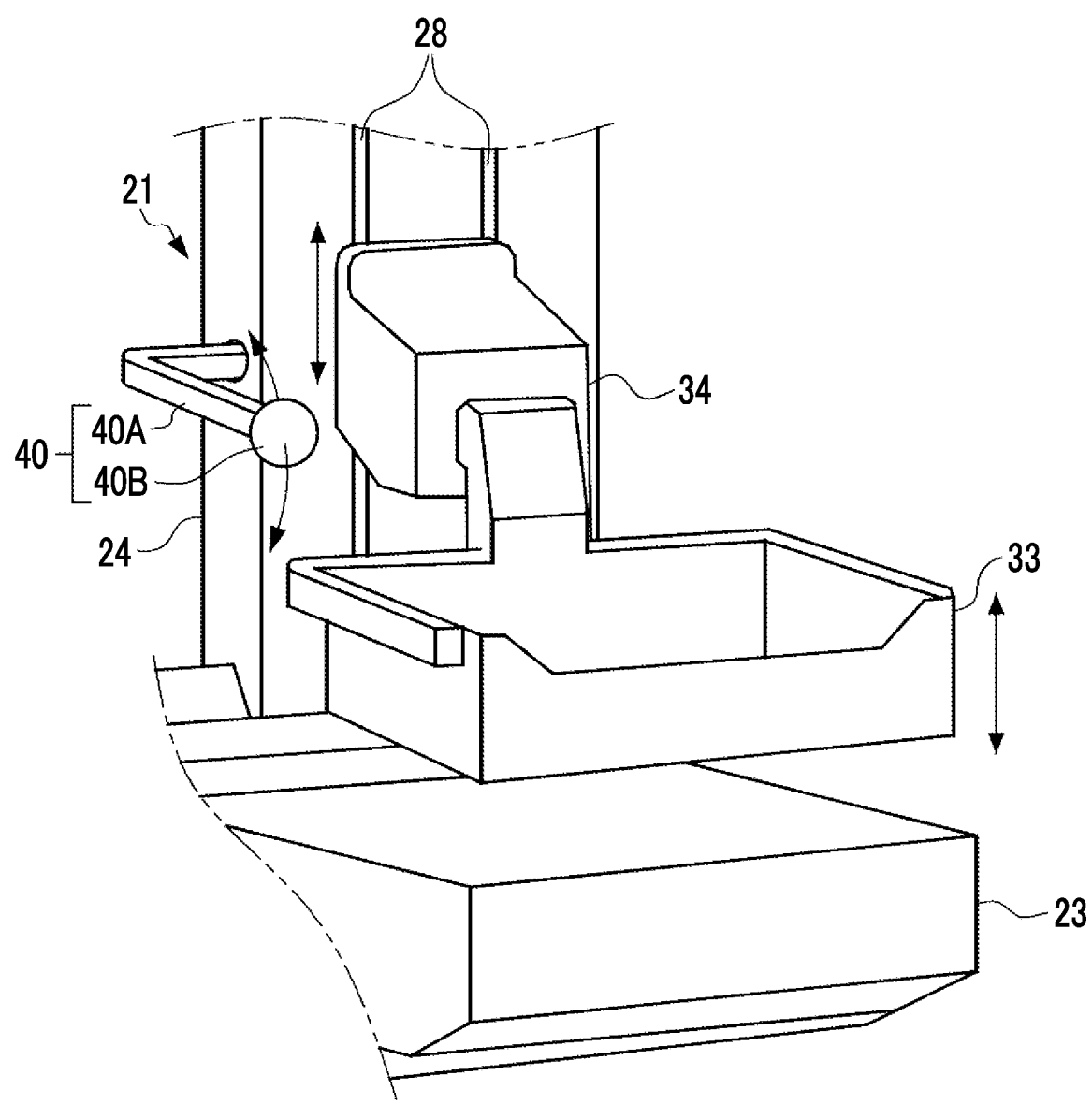
FIG. 34 is a partially enlarged view of the mammography apparatus in which the operation portion is provided on a support portion.

FIG. 34 shows an example in which the operation portion 40 is provided on the body portion 24 of the arm 21 as a support portion. As in the first embodiment, the operation portion 40 includes the main shaft portion 40A and the grip portion 40B. In the present example, the main shaft portion 40A is bent in an L shape, and the base end side is rotatably connected to a side surface of the body portion 24. The free end side of the main shaft portion 40A stretches toward the side of the subject who places the breast M on the imaging table 23.

The operator can move the compression plate 33 in the vertical direction by displacing the grip portion 40B provided on the free end side of the main shaft portion 40A in the vertical direction. In FIG. 34, the operation portion 40 is provided on a left side of the body portion 24 as viewed from a front side of the mammography apparatus 10, but the operation portion 40 may be provided on a right side of the body portion 24 or may be provided on both the right and left sides.

Note that it is also possible to provide the operation portion shown in the second to fourth modification examples on the support portion.

Other Modification Examples

In the embodiments described above and each modification example, various operation portions are shown, but the operation portion need only be a cantilever type lever having one end, which is the free end, and at least the free end need only be displaced along the movement direction of the compression plate. The displacement of the free end and the movement of the compression plate do not necessarily have to be in the same direction, and a form may be adopted in which the free end rotates and the compression plate is moved in a linear direction as described above.

In addition, a form may be adopted in which the operation portion does not rotate around the base end and is displaced in the linear direction in the vertical direction. In this case, the displacement direction of the operation portion completely coincides with the movement direction of the compression plate. In a case in which such an operation portion that is displaced in the linear direction is used, the displacement amount detected by the displacement amount detection unit 63 described above corresponds to a slide movement amount, not the angle. In addition, the displacement speed detected by the displacement speed detection unit 65 corresponds to the speed, not the angular speed. In addition, although a form of the lever has been described as an example of the operation portion, for example, a slide type switch can be used as the operation portion. In this case, the switch need only be disposed such that a sliding direction of the switch and the movement direction of the compression plate coincide with each other.

In addition, although the stretching direction of the operation portion has been described with an example of the anteroposterior direction (corresponding to the depth direction) of the mammography apparatus 10, a form may be adopted in which the stretching direction stretches in the width direction of the mammography apparatus 10. Note that the lateral direction is a direction that intersects (for example, orthogonal to) the anteroposterior direction and the vertical direction. In addition, in a case of a form in which the stretching direction of the operation portion stretches in the lateral direction, it is preferable to provide two operation portions of a first operation portion that stretches in a right side of the subject and a second operation portion that stretches in a left side. The first operation portion and the second operation portion are provided on, for example, a right side surface and a left side surface of the movable portion 34, respectively.

In addition, in the embodiments described above and each modification example, the drive mechanism 50 is configured by the actuator using the rod screw, but it can also be configured by a belt type actuator. Further, a mechanical manual type movement mechanism can be used instead of the drive mechanism 50. The belt type actuator and the manual type movement mechanism are known, for example, in JP2010-179030A.

In addition, each of the embodiments described above and each modification example can be combined with each other as long as there is no contradiction.

In each of the embodiments described above and each modification examples, the following various processors can be used as a hardware structure of the controller using the processor 60 as an example. Various processors described above include the CPU, which is a general-purpose processor that functions by executing a software (program), as well as a processor such as a field programmable gate array (FPGA) of which a circuit configuration can be changed after manufacturing. The FPGA includes a dedicated electric circuit, which is a processor having a circuit configuration specially designed for executing a specific process such as a programmable logic device (PLD) or an application specific integrated circuit (ASIC).

The controller may be configured by one of these various processors or a combination of two or more processors of the same type or different types (for example, a combination of a plurality of the FPGAs, or a combination of the CPU and the FPGA). In addition, a plurality of the controllers may be configured by one processor.

There are a plurality of examples in which the plurality of controllers are configured by one processor. As a first example, as represented by a computer such as a client computer or a server, there is a form in which one processor is configured by a combination of one or more CPUs and software, and the processor functions as the plurality of controllers. As a second example, as represented by a system on chip (SOC), there is a form in which the processor that realizes the functions of the entire system including the plurality of controllers by one IC chip is used. Thus, the controller can be configured by one or more of the various processors described above as the hardware structure.

Further, as the hardware structure of these various processors, more specifically, an electric circuit in which circuit elements such as semiconductor elements are combined can be used.

The technology of the present disclosure can also be appropriately combined with the various embodiments described above and/or various modification examples. Further, it is needless to say that the present disclosure is not limited to each of the embodiments described above, various configurations can be adopted as long as the configuration does not deviate from the gist.

The contents described and shown above are the detailed description of the parts relating to the technology of the present disclosure, and are merely an example of the technology of the present disclosure. For example, the above description of the configuration, the function, the action, and the effect are the description of examples of the configuration, the function, the action, and the effect of the parts relating to the technology of the present disclosure. Therefore, it is needless to say that unnecessary parts may be deleted, new elements may be added, or replacements may be made with respect to the contents described and shown above within a range that does not deviate from the gist of the technology of the present disclosure. In addition, in order to avoid complications and facilitate understanding of the parts relating to the technology of the present disclosure, in the contents described and shown above, the description of common general knowledge and the like that do not particularly require description for enabling the implementation of the technology of the present disclosure are omitted.

All of the documents, the patent applications, and the technical standards described in the present specification are incorporated in the present specification by reference to the same extent as a case in which each of the document, the patent application, and the technical standard is specifically and individually described to be incorporated by reference.

What is claimed is:

1. A mammography apparatus comprising:
    an imaging table on which a breast of a subject is placed;
    a compression plate that compresses the breast, the compression plate being disposed to face the imaging table and being movable in a vertical direction with respect to the imaging table;
    an operation portion that is operated to move the compression plate, the operation portion being provided separately from the compression plate and being displaced along a movement direction of the compression plate;
    an actuator that drives the compression plate;
    a displacement amount detection unit that detects a displacement amount of the operation portion; and a processor that controls the actuator based on the displacement amount detected by the displacement amount detection unit, wherein the compression plate is moved by driving force generated by the actuator.

2. The mammography apparatus according to claim 1, further comprising:

a support portion that supports the compression plate to be movable with respect to the imaging table, wherein the operation portion is provided on the support portion.

3. The mammography apparatus according to claim 1, further comprising:

a support portion that supports the compression plate to be movable with respect to the imaging table; and a movable portion that is disposed between the compression plate and the support portion and is moved in the vertical direction together with the compression plate, wherein the operation portion is provided on the movable portion.

4. The mammography apparatus according to claim 1, wherein the processor changes a movement speed of the compression plate based on the displacement amount detected by the displacement amount detection unit.

5. The mammography apparatus according to claim 1, further comprising:

a height detection unit that detects a height of the compression plate with respect to the imaging table, wherein the processor changes a movement speed of the compression plate in response to the height of the compression plate.

6. The mammography apparatus according to claim 5, wherein the processor sets an initial speed of the compression plate in a case in which the compression plate is raised from a state in which the compression plate is positioned at a relatively low position to be faster than an initial speed of the compression plate in a case in which the compression plate is raised from a state in which the compression plate is positioned at a relatively high position.

7. The mammography apparatus according to claim 5, wherein the processor sets an initial speed of the compression plate in a case in which the compression plate is lowered from a state in which the compression plate is positioned at a relatively high position to be faster than an initial speed of the compression plate in a case in which the compression plate is lowered from a state in which the compression plate is positioned at a relatively low position.

8. The mammography apparatus according to claim 1, further comprising:

a displacement speed detection unit that detects a displacement speed of the operation portion, wherein the processor sets a movement speed of the compression plate to be faster as the displacement speed of the operation portion is faster.

9. The mammography apparatus according to claim 1, further comprising:

a pressure detection unit that detects a pressure received by the compression plate from the breast.

10. The mammography apparatus according to claim 9, wherein the processor sets a rate of change in speed, which is a ratio of a change amount of a movement speed of the compression plate to a unit displacement amount of the operation portion, to be smaller as the pressure is larger.

11. The mammography apparatus according to claim 9, wherein the processor stops movement of the compression plate in a case in which the pressure detected by the pressure detection unit is equal to or larger than a preset threshold value.

12. The mammography apparatus according to claim 1, further comprising:

a load increasing unit that increases a load for operating the operation portion as a displacement amount of the operation portion is larger.

13. The mammography apparatus according to claim 1, wherein the operation portion is a cantilever type lever having one end, which is a free end, and at least the free end is displaced along the movement direction of the compression plate.

14. The mammography apparatus according to claim 13, wherein assuming that a direction of a position of the subject who places the breast on the imaging table is anterior and an opposite direction thereof is posterior, the operation portion stretches in an anteroposterior direction or a lateral direction.

15. The mammography apparatus according to claim 13, wherein the operation portion rotates about a fulcrum provided on a base end side.

16. The mammography apparatus according to claim 15, wherein the operation portion includes a main shaft portion that extends from the base end side to a free end side, and a protruding portion that is provided on the main shaft portion and protrudes to at least one of a lower side or an upper side with an axial direction of the main shaft portion as a reference.

17. The mammography apparatus according to claim 16, wherein the protruding portion includes a first protruding portion that protrudes to the lower side of the main shaft portion, and a second protruding portion that protrudes to the upper side of the main shaft portion.

18. The mammography apparatus according to claim 16, wherein the protruding portion has a hook shape or a ring shape.

* * * * *